(12) United States Patent
Shelton, IV

(10) Patent No.: US 7,140,528 B2
(45) Date of Patent: Nov. 28, 2006

(54) SURGICAL STAPLING INSTRUMENT HAVING AN ELECTROACTIVE POLYMER ACTUATED SINGLE LOCKOUT MECHANISM FOR PREVENTION OF FIRING

(75) Inventor: Frederick E. Shelton, IV, Hillsboro, OH (US)

(73) Assignee: Ethicon Endo-Surgery, Inc., Cincinatti, OH (US)

( * ) Notice: Subject to any disclaimer, the term of this patent is extended or adjusted under 35 U.S.C. 154(b) by 91 days.

(21) Appl. No.: 11/066,371

(22) Filed: Feb. 25, 2005

(65) Prior Publication Data

US 2005/0173490 A1    Aug. 11, 2005

Related U.S. Application Data

(63) Continuation-in-part of application No. 10/441,424, filed on May 20, 2003, now Pat. No. 7,044,352.

(60) Provisional application No. 60/591,694, filed on Jul. 28, 2004.

(51) Int. Cl.
*A61B 17/068* (2006.01)

(52) U.S. Cl. ........................ 227/175.4; 227/175.2; 227/182.1; 227/19

(58) Field of Classification Search .. 227/175.1–175.4, 227/19, 182.1; 606/218–220, 142, 143, 75
See application file for complete search history.

(56) References Cited

U.S. PATENT DOCUMENTS

| | | | |
|---|---|---|---|
| 5,031,814 A | 7/1991 | Tompkins et al. | |
| 5,071,052 A | 12/1991 | Rodak et al. | |
| 5,137,198 A | 8/1992 | Nobis et al. | |
| 5,397,046 A | 3/1995 | Savage et al. | |
| 5,413,267 A | 5/1995 | Solyntjes et al. | |
| 5,413,268 A | 5/1995 | Green et al. | |
| 5,445,304 A | 8/1995 | Plyley et al. | |
| 5,465,895 A | 11/1995 | Knodel et al. | |
| 5,484,095 A | 1/1996 | Green et al. | |
| 5,535,937 A | 7/1996 | Boiarski et al. | |
| 5,562,239 A * | 10/1996 | Boiarski et al. | 227/175.2 |
| 5,584,425 A | 12/1996 | Savage et al. | |
| 5,680,983 A | 10/1997 | Plyley et al. | |
| 5,693,042 A * | 12/1997 | Boiarski et al. | 606/10 |
| 5,709,334 A | 1/1998 | Sorrentino et al. | |
| 5,735,445 A | 4/1998 | Vidal et al. | |
| 5,779,130 A * | 7/1998 | Alesi et al. | 227/176.1 |
| 5,918,791 A | 7/1999 | Sorrentino et al. | |
| 5,959,852 A * | 9/1999 | Deloy et al. | 363/45 |
| 6,010,054 A | 1/2000 | Johnson et al. | |
| 6,032,849 A | 3/2000 | Mastri et al. | |
| 6,079,606 A | 6/2000 | Milliman et al. | |

(Continued)

*Primary Examiner*—Scott A. Smith
*Assistant Examiner*—Gloria R. Weeks
(74) *Attorney, Agent, or Firm*—Dean L. Garner

(57) ABSTRACT

A surgical instrument includes an E-beam firing bar engages the channel and selectively engages the anvil during distal firing movements, wherein the tissue is severed and stapled driven upward from the staple cartridge to form against the anvil. In particular, a wedge integral to the staple cartridge is driven distally by a middle pin of the firing bar to effect stapling. A single lockout of the staple channel responds to the presence of the wedge sled in its unfired position to allow the firing bar to fire. Otherwise, the single lockout prevents firing when the staple cartridge is missing or spent. Further, some versions include an Electroactive Polymer (EAP) actuator that presents an abutting surface, or acts as a trapdoor to a ramped recess in a staple channel to block the firing bar, as an active approach to preventing firing for one or more conditions.

18 Claims, 30 Drawing Sheets

U.S. PATENT DOCUMENTS

| | | |
|---|---|---|
| 6,109,500 A | 8/2000 | Alli et al. |
| 6,202,914 B1 | 3/2001 | Geiste et al. |
| 6,667,825 B1 | 12/2003 | Lu et al. |
| 7,044,352 B1 * | 5/2006 | Shelton et al. ........... 227/175.1 |
| 2001/0029384 A1 | 10/2001 | Nicholas et al. |
| 2002/0165541 A1 * | 11/2002 | Whitman .................... 606/48 |
| 2004/0232195 A1 | 11/2004 | Shelton et al. |
| 2006/0022015 A1 * | 2/2006 | Shelton et al. ........... 227/176.1 |
| 2006/0025812 A1 * | 2/2006 | Shelton, IV ................ 606/205 |

* cited by examiner

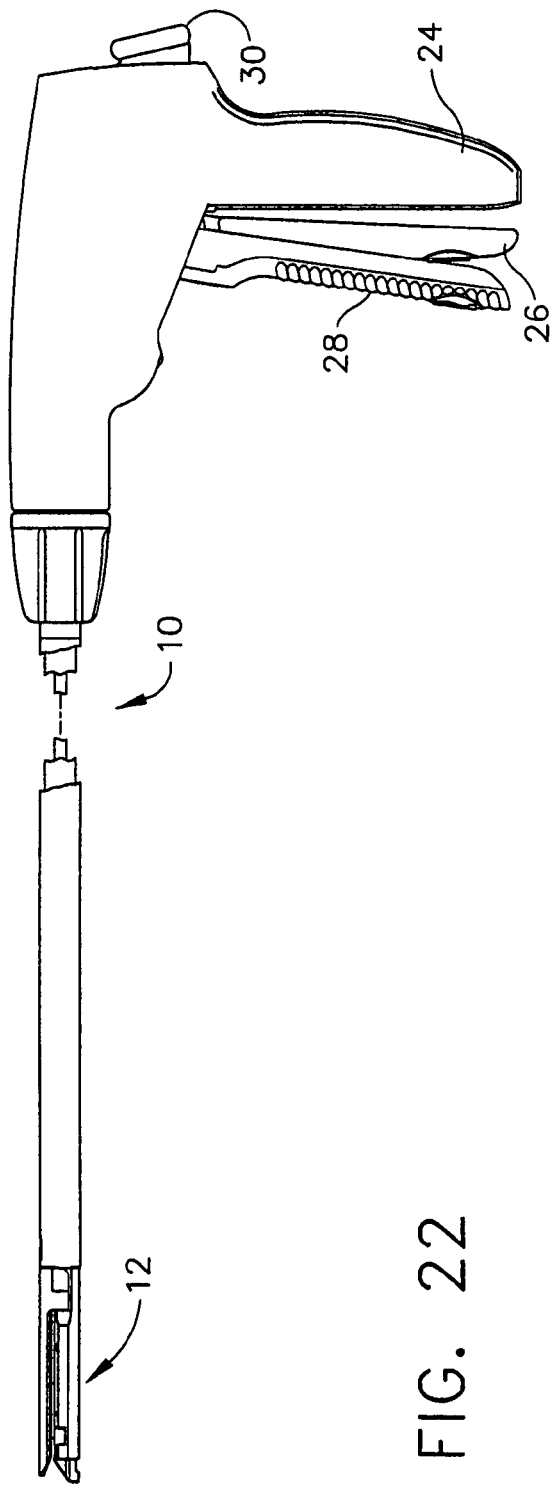
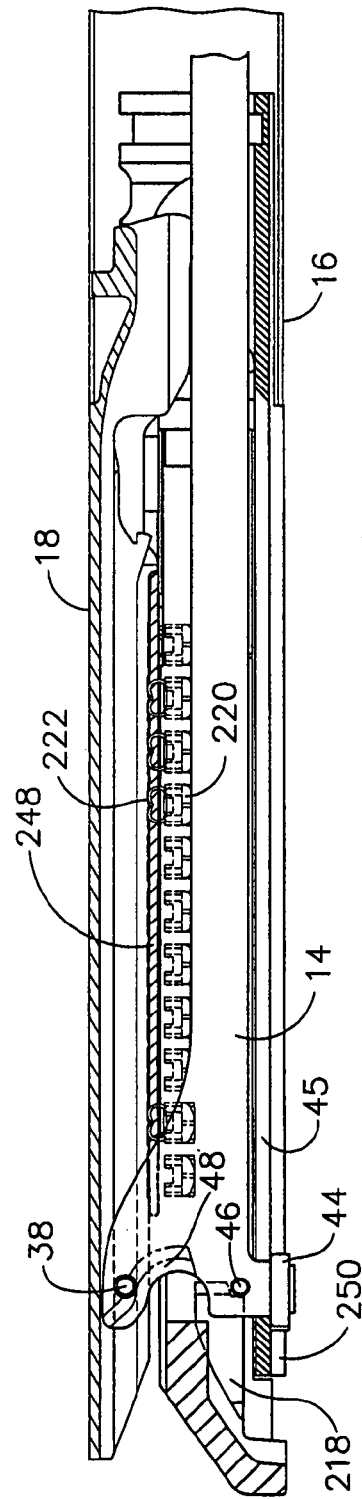
FIG. 22
FIG. 23

SURGICAL STAPLING INSTRUMENT HAVING AN ELECTROACTIVE POLYMER ACTUATED SINGLE LOCKOUT MECHANISM FOR PREVENTION OF FIRING

CROSS REFERENCE TO RELATED APPLICATIONS

The present application is a continuation in part of U.S. patent application Ser. No. 10/441,424, U.S. patent application Ser. No. 7,044,352 filed 20 May 2003, entitled "SURGICAL STAPLING INSTRUMENT HAVING A SINGLE LOCKOUT MECHANISM FOR PREVENTION OF FIRING" to Frederick E. Shelton IV, Michael Earl Setser, and William Bruce Weisenburgh II, the disclosure of which is hereby incorporated by reference in its entirety.

This application claims the benefit of U.S. provisional application Ser. No. 60/591,694, entitled "SURGICAL INSTRUMENT INCORPORATING AN ELECTRICALLY ACTUATED ARTICULATION MECHANISM" to Shelton IV, filed 28 Jul. 2004.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

An example of a surgical stapler suitable for endoscopic applications is described in U.S. Pat. No. 5,465,895, which advantageously provides distinct closing and firing actions. Thereby, a clinician is able to close the jaw members upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

It is often advantageous to build an end effector for the surgical stapler that is reusable. For instance, one patient may need a series of severing and stapling operations. Replacing an entire end effector for each operation tends to be economically inefficient. This is especially true if the end effector is built to be strong and reliable over repeated operations. To that end, staple cartridges are fitted into the end effector prior to each operation of the surgical stapler. Thus, a much smaller amount of the surgical staples is discarded after each use.

While the staple cartridge provides numerous advantages, it is desirable to prevent inadvertent firing of the surgical stapler when an unfired staple cartridge is not present. Otherwise, the severing of tissue may occur without the staples to minimize bleeding. It is particularly desirable that preventing such inadvertent firing be accomplished in a reliable way that is not subject to an intervening malfunction. Moreover, for ease of manufacturing and assembly, it is further desirable that the lockout features be accomplished with a minimum number of components.

In U.S. Pat. No. 6,202,914 to Geiste, a locking mechanism is disclosed that includes a firing bar ("actuation channel") and includes a pair of integral cam wedges that actuate a staple cartridge. An inverted T-shaped member rides under and between the cam wedges to prevent a hook from catching an edge of the firing bar. Once advanced distally, the inverted T-shaped member remains as the firing bar is retracted and thus would be locked out if advanced a second time.

While such a lockout mechanism provides certain advantages, it is desirable to incorporate a lockout into a surgical severing and stapling mechanism that operates within an E-beam firing bar that has advantages of its own. In particular, the E-beam engages the lower jaw (staple channel) and the upper jaw (anvil) during firing, assisting in a consistent spacing of jaws. It would be further desirable to have a lockout mechanism that may be remotely controlled so that additional lockout conditions may be incorporated.

Consequently, a significant need exists for an improved surgical stapling and severing instrument that prevents inadvertent firing (i.e., severing and stapling) when a staple cartridge is not installed or is spent, having been previously fired.

BRIEF SUMMARY OF THE INVENTION

The invention overcomes the above-noted and other deficiencies of the prior art by providing a single lockout mechanism that prevents firing a surgical stapling and severing instrument when either a staple cartridge is not installed or is spent. In particular, the single lock mechanism prevents distal movement of a firing bar, and thus severing of tissue, in instances where simultaneous stapling would not occur.

In one aspect of the invention, a surgical instrument includes a handle portion operable to produce a firing motion that actuates an implement portion. A lockout member is positioned within the implement portion to block this firing motion. An electroactive polymer (EAP) actuator may be selectively energized from the handle portion or other remote location to move the lockout member out of an obstructing position, allowing firing. Thereby, a lockout mechanism may be responsive to a range of conditions to prevent an inadvertent firing.

In another aspect of the invention, a surgical instrument that includes upper and lower jaws for clamping, severing and stapling tissue by receiving a firing bar advantageously includes a lockout device positioned within the implement portion to block this firing motion when conditions requisite to firing are not present. Thereby, inadvertent severing is prevented when effective stapling is not assured.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 22 depicts a partially cutaway side elevation view of the surgical stapling and severing instrument of FIG. 1 in a fully fired position.

FIG. 23 depicts a view in centerline section of the distal end of the surgical stapling and severing instrument of FIG. 1 in a fully fired position.

DETAILED DESCRIPTION OF THE INVENTION

Figure 1:
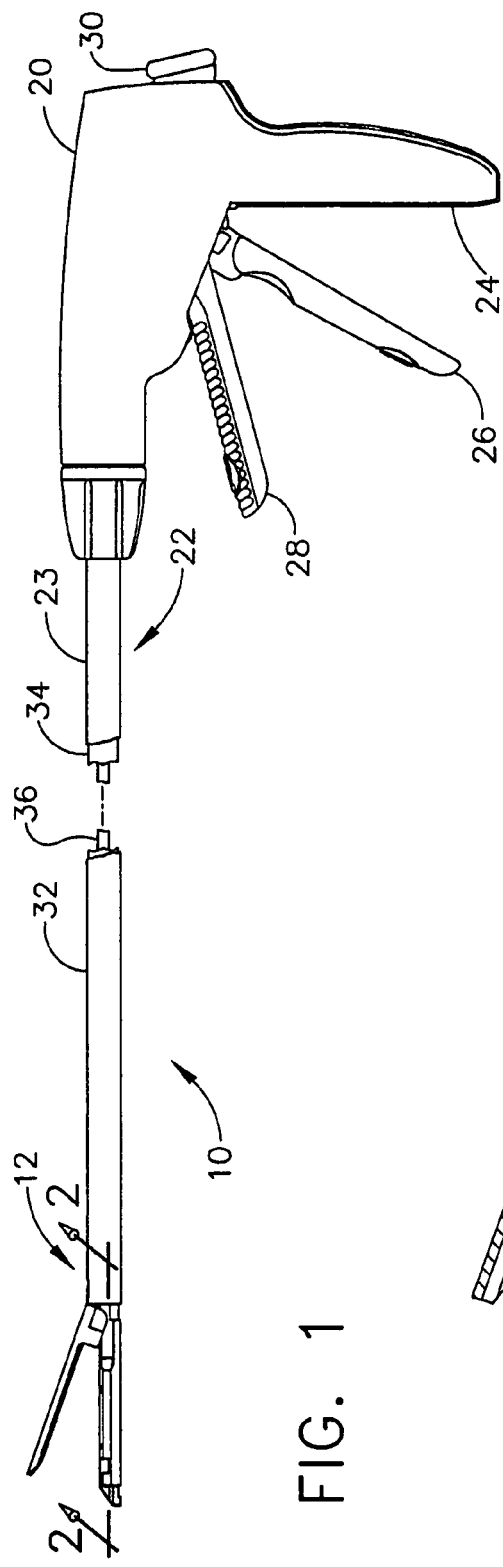
FIG. 1 depicts a partially cutaway side elevation view of a surgical stapling and severing instrument in an open position.
Figure 2:
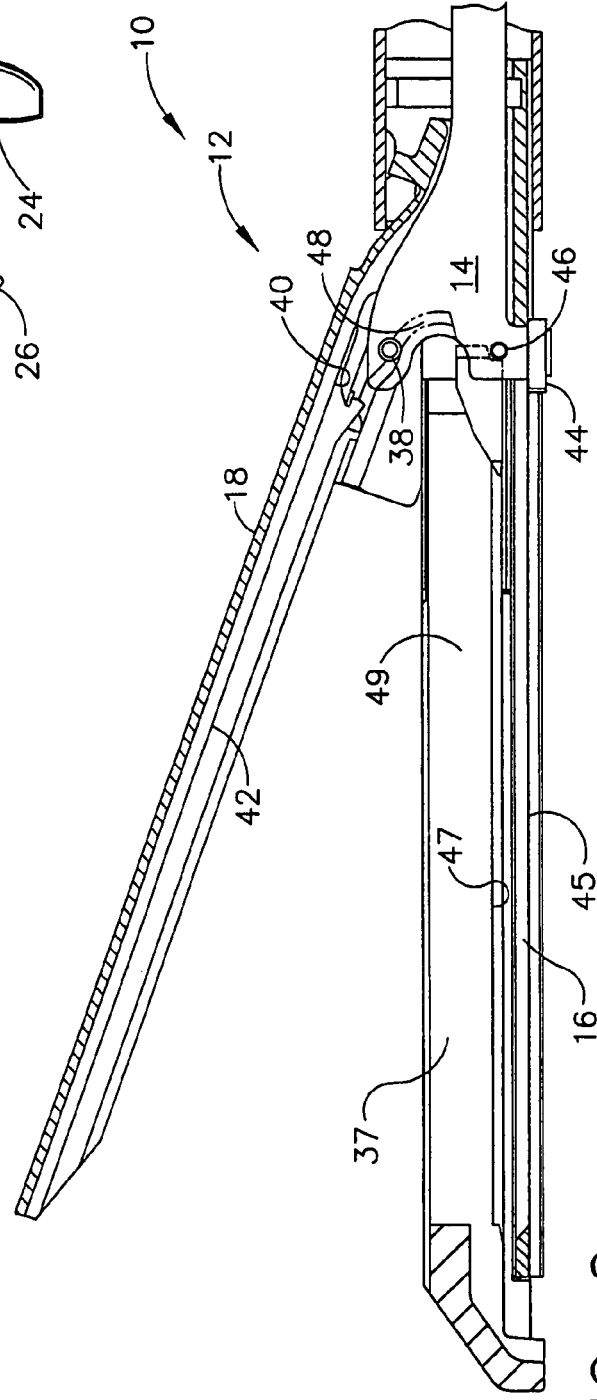
FIG. 2 depicts a cross-sectional side elevation detail view along the line 2—2 of FIG. 1 of an end effector of the surgical stapling and severing instrument.

Turning to the Drawings, wherein like numerals denote like components throughout the several views, FIGS. 1 and 2 depict a surgical stapling and severing instrument 10 that is capable of practicing the unique benefits of the present invention. The surgical stapling and severing instrument 10 incorporates an end effector 12 having an E-beam firing mechanism ("firing bar") 14 that advantageously controls the spacing of the end effector 12. In particular, an staple channel 16 and a pivotally translatable anvil 18 are maintained at a spacing that assures effective stapling and severing. Furthermore, firing (i.e., severing and stapling) is prevented from occurring if the instrument is not capable of stapling with a single lockout mechanism, which is described in more detail below.

The surgical and stapling and severing instrument 10 includes a handle portion 20 connected to an implement portion 22, the latter further comprising a shaft 23 distally terminating in the end effector 12. The handle portion 20 includes a pistol grip 24 toward which a closure trigger 26 is pivotally drawn by the clinician to cause clamping or closing of the anvil 18 toward the staple channel 16 of the end effector 12. A firing trigger 28 is farther outboard of the closure trigger 26 and is pivotally drawn by the clinician to cause the stapling and severing of clamped tissue in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that, for convenience and clarity, spatial terms such as "vertical" and "horizontal" are used herein with respect to the drawings. However, surgical instruments are used in many orientations and positions, and these terms are not intended to be limiting and absolute.

Closure trigger 26 is actuated first. Once the clinician is satisfied with the positioning of the end effector 12, the clinician may draw back the closure trigger 26 to its fully closed, locked position proximate to the pistol grip 24. The firing trigger 28 is then actuated. The firing trigger 28 springedly returns when the clinician removes pressure. A release button 30, when depressed on the proximal end of the handle portion 20, releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the staple channel 16 and translating proximally with the closure sleeve 32.

The staple channel 16 receives a staple device, depicted as a staple cartridge 37, that is responsive to the firing bar 14 to drive staples into forming contact with the anvil 18. It will appreciated that although a readily replaceable staple cartridge 37 is advantageously described herein, a staple cartridge 37 consistent with aspects of the present invention may be permanently affixed or integral to the staple channel 16, for instance when a larger portion of the end effector 12 is replaced after each firing.

It should be appreciated that a staple device consistent with applications of the present invention may be integral with the staple channel 16 rather than being advantageously detachable therefrom.

E-Beam Firing Mechanism

Figure 3:
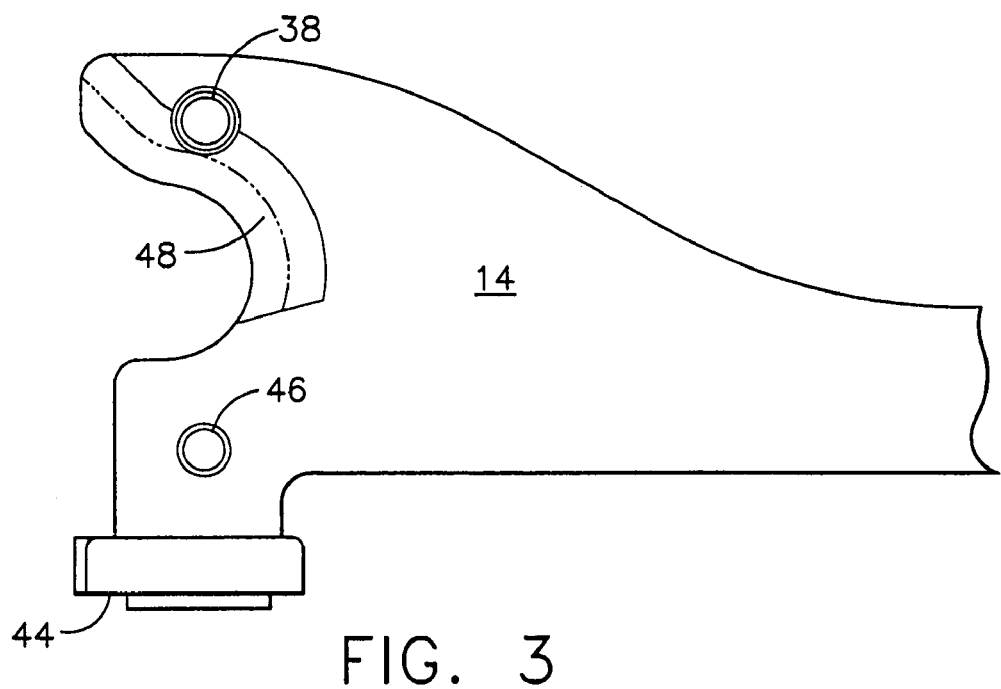
FIG. 3 depicts an enlarged side elevation view of the firing bar of the surgical stapling and severing instrument of FIG. 2.
Figure 4:
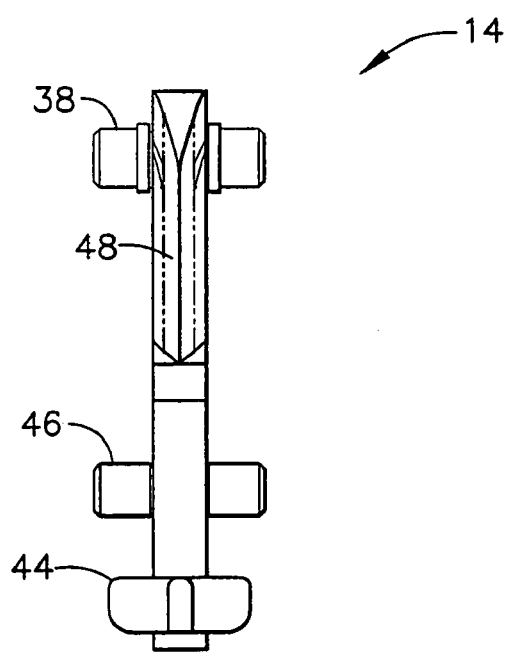
FIG. 4 depicts an enlarged front view of the firing bar of the surgical stapling and severing instrument of FIG. 2.

With particular reference to FIGS. 2–4, the firing bar 14 includes three vertically-spaced pins that control the spacing of the end effector 12 during firing. In particular, an upper pin 38 is staged to enter an anvil pocket 40 near the pivot between the anvil 18 and staple channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38.

Firing bar 14 also includes a lower most pin, or firing bar cap, 44 that upwardly engages a channel slot 45 in the staple channel 16, thereby cooperating with the upper pin 38 to draw the anvil 18 and the staple channel 16 slightly closer together in the event of excess tissue clamped therebetween.

Figure 5:
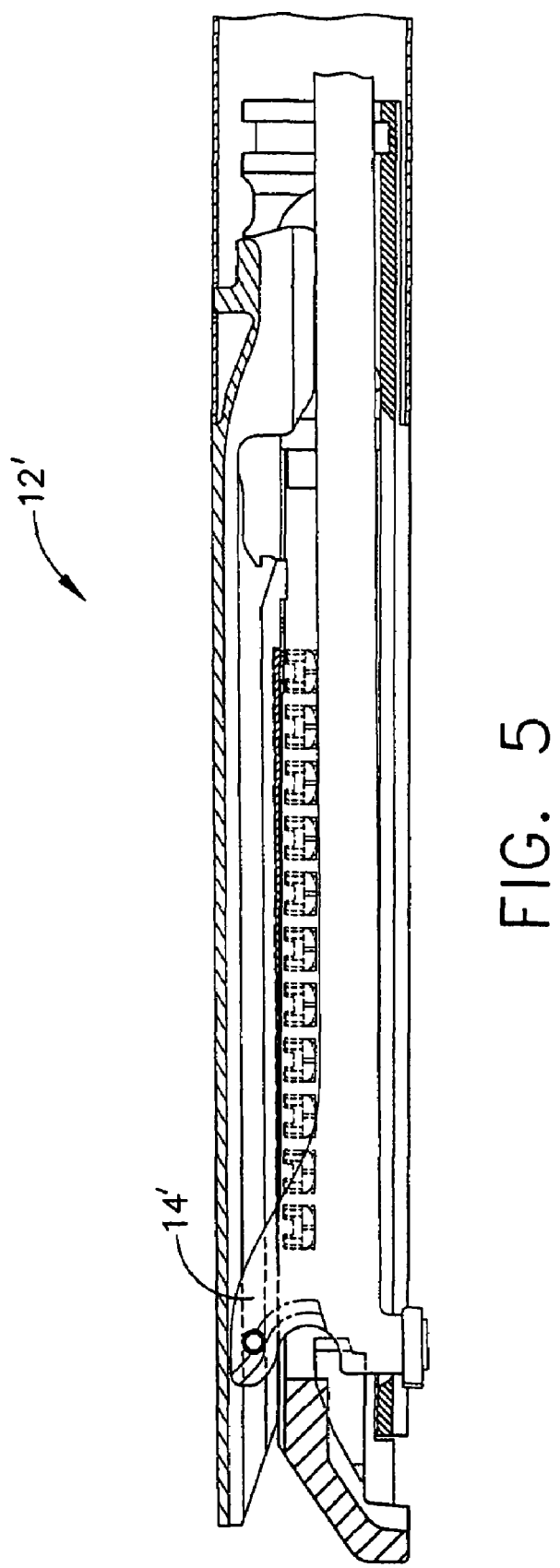
FIG. 5 depicts a cross-sectional side elevation detail view of an alternative end effector for the surgical stapling and severing instrument of FIG. 1, incorporating a firing bar that lacks a middle pin for preventing pinching of the end effector.

The firing bar 14 advantageously includes a middle pin 46 that passes through a firing drive slot 47 formed in a lower surface of the cartridge 37 and an upward surface of the staple channel 16, thereby driving the staples therein as described below. The middle pin 46, by sliding against the staple channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2–4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14, with regard to the staple channel 16 and anvil 18, assure that an effective cut is performed.

Cambered Anvil with Selected Cartridge Gap

The affirmative vertical spacing provided by the E-Beam firing bar 14 is suitable for the limited size available for endoscopic devices. Moreover, the E-Beam firing bar 14 enables fabrication of an anvil 16 with a camber imparting a vertical deflection at its distal end, similar to the position depicted in FIG. 5. This cambered anvil 16 advantageously assists in achieving the desired gap in the end effector 12 even with an anvil 16 reduced thickness, which is thus more suited to the size limitations of an endoscopic device.

The E-Beam firing bar 14 further enables increased applications, especially in combination with a range of configurations of staple cartridges. For instance, a clinician may select a gray staple cartridge yielding a 0.02 mm tissue gap, a white staple cartridge yielding a 0.04 mm tissue gap, a blue cartridge yielding a 0.06 mm tissue gap, or a green cartridge yielding a 0.10 mm tissue gap. The vertical height of each respective staple cartridge in combination with the length of staples and an integral wedge sled (described in more detail below) predetermines this desired tissue thickness with the anvil 18 appropriately vertically spaced by the E-Beam firing bar 14.

Two-Axis Handle

With reference to FIGS. 6–9, the handle portion 20 is comprised of first and second base sections 50 and 52, which are molded from a polymeric material such as a glass-filled polycarbonate. The first base section 50 is provided with a plurality of cylindrical-shaped pins 54. The second base section 52 includes a plurality of extending members 56, each having a hexagonal-shaped opening 58. The cylindrical-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6–9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72 extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the staple channel 16 of the end effector 12 and proximal movement effects closing, as discussed below.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 110 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30.

Figure 8:
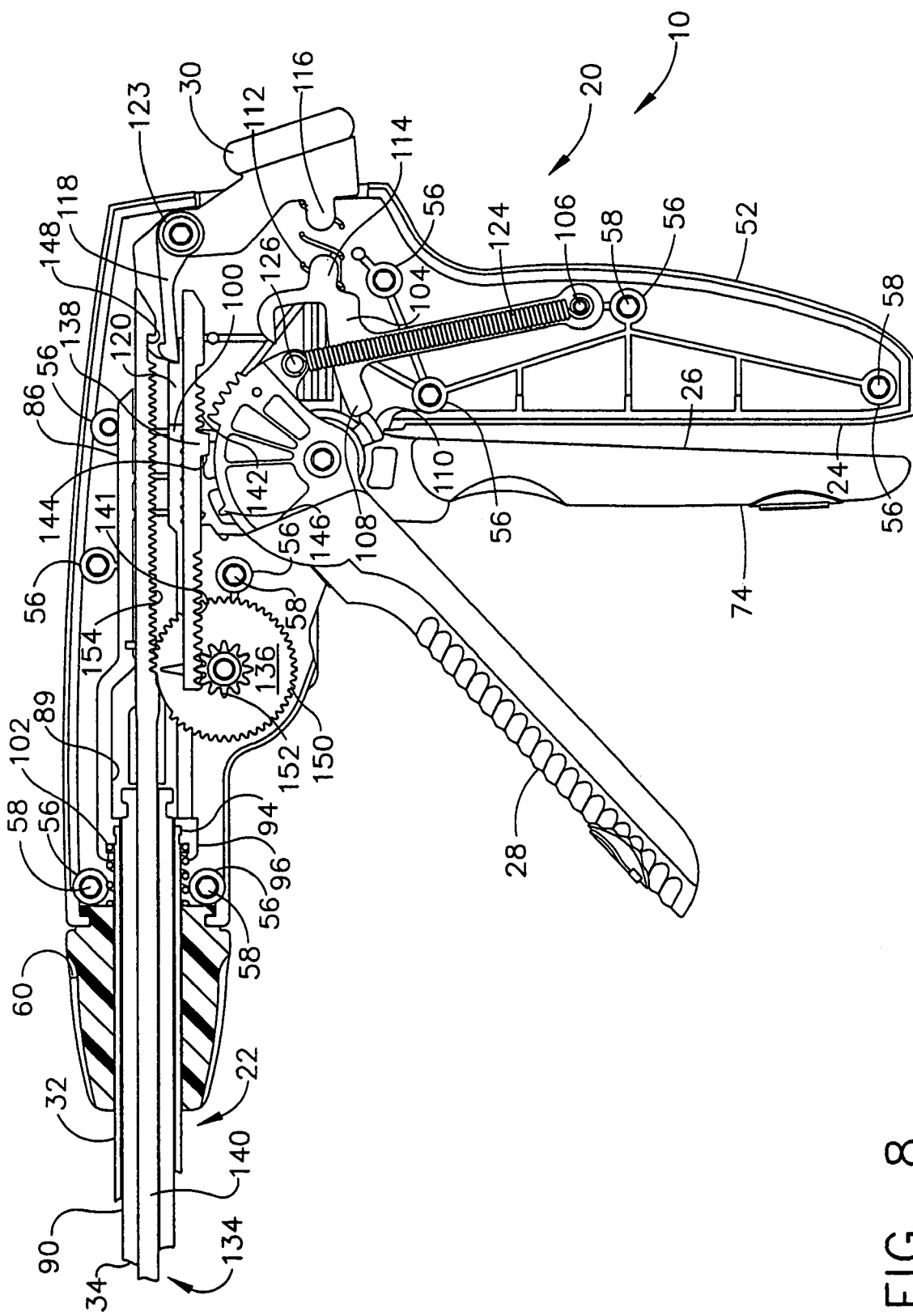
FIG. 8 depicts a side elevational view of the handle portion of the proximal end of the surgical stapling and severing instrument of FIG. 1 with the-left side removed to expose interior parts in the closed ("clamped") position.

As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28, biasing front surface 130 of closure trigger 26.

As the closure trigger 26 is moved toward the pistol grip 24, its front surface 130 engages with the engaging surface 128 on the firing trigger 28, causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIG. 6–9) and a metal drive rod 140.

The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position.

The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
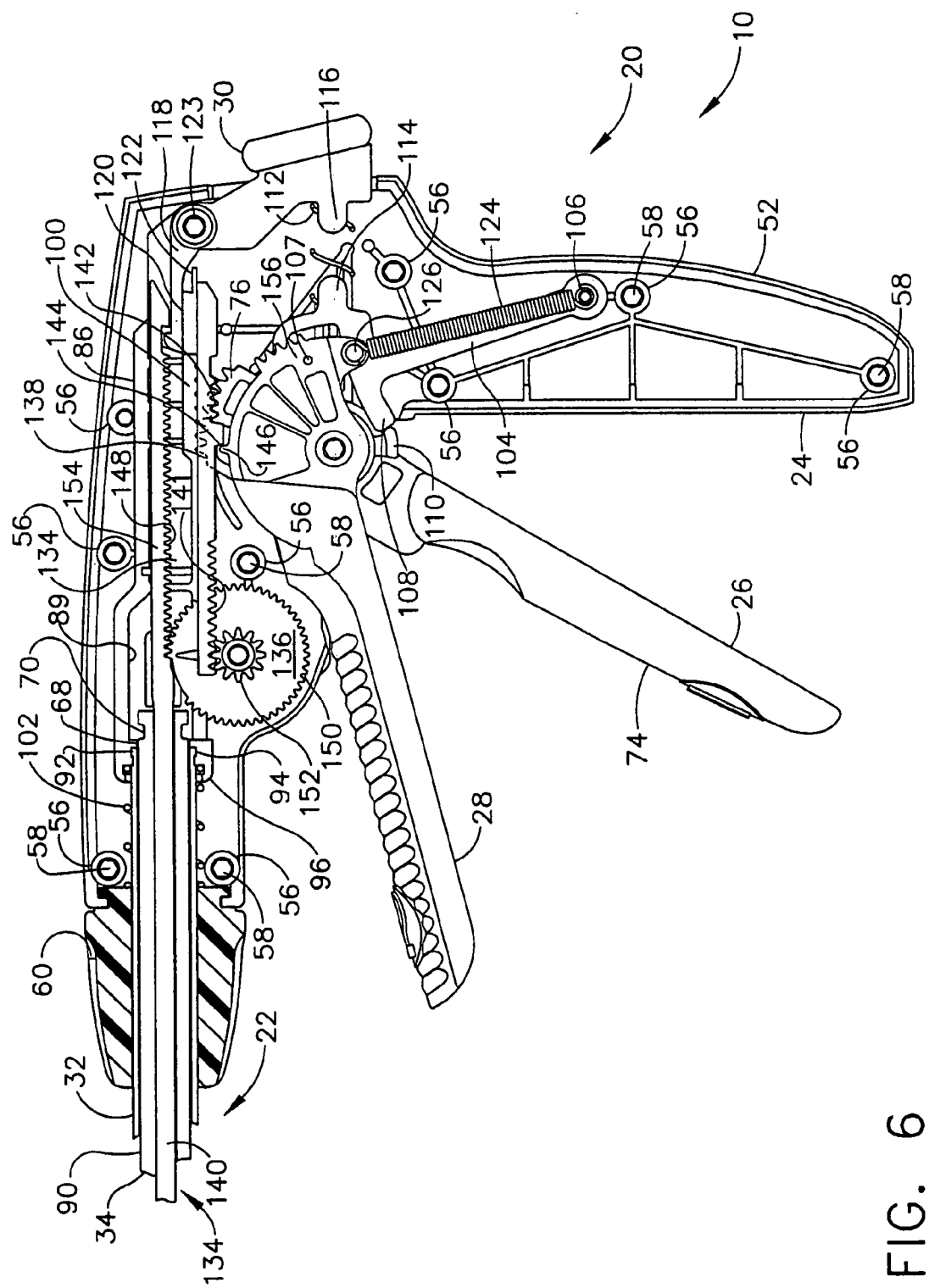
FIG. 6 depicts a side elevational view of a handle portion of a proximal end of the surgical stapling and severing instrument of FIG. 1 with a left side removed to expose interior parts in an unclamped, unfired ("start") position.
Figure 7:
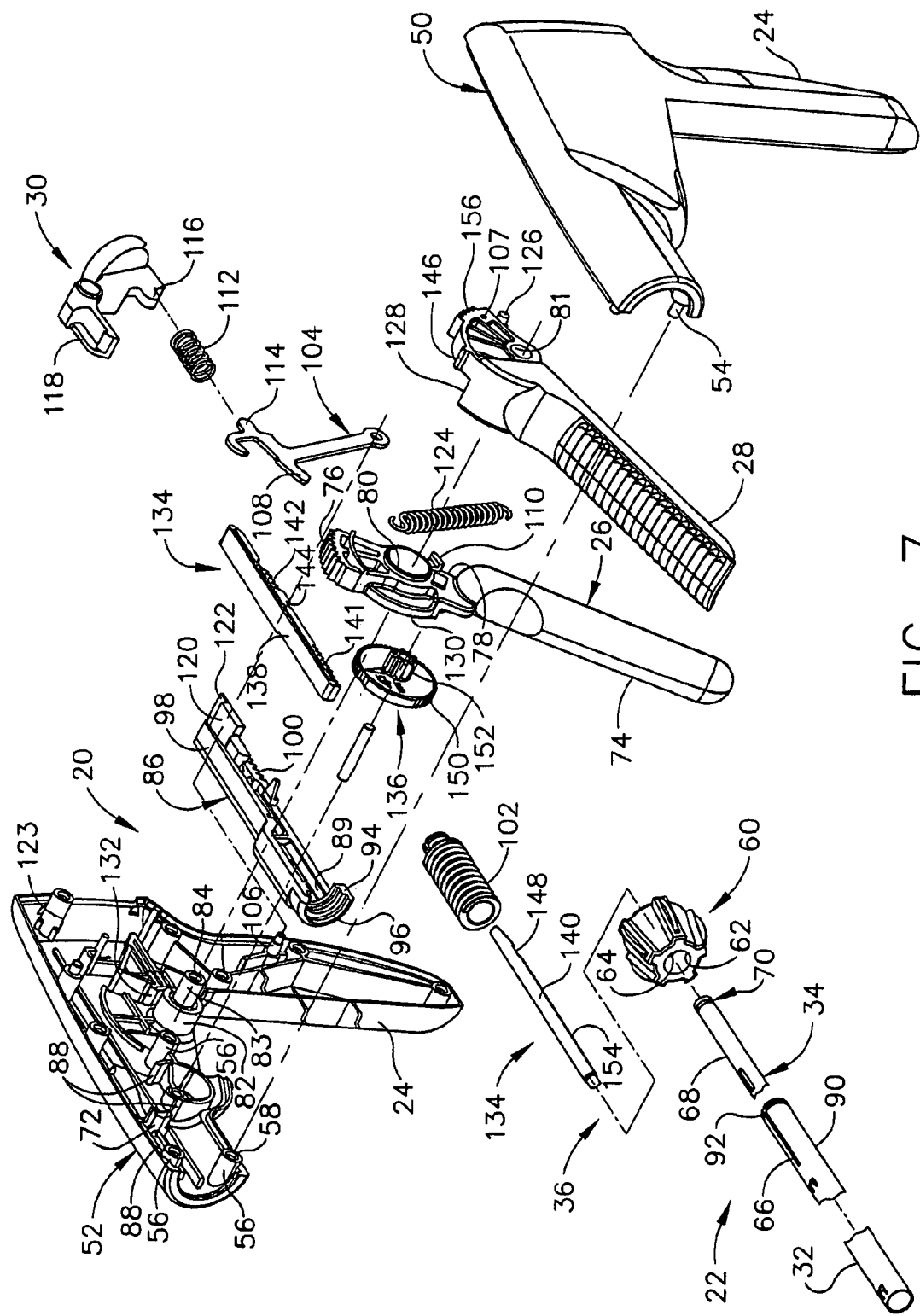
FIG. 7 depicts a perspective, exploded view of the handle portion of the proximal end of the surgical stapling and severing instrument of FIG. 1.
Figure 9:
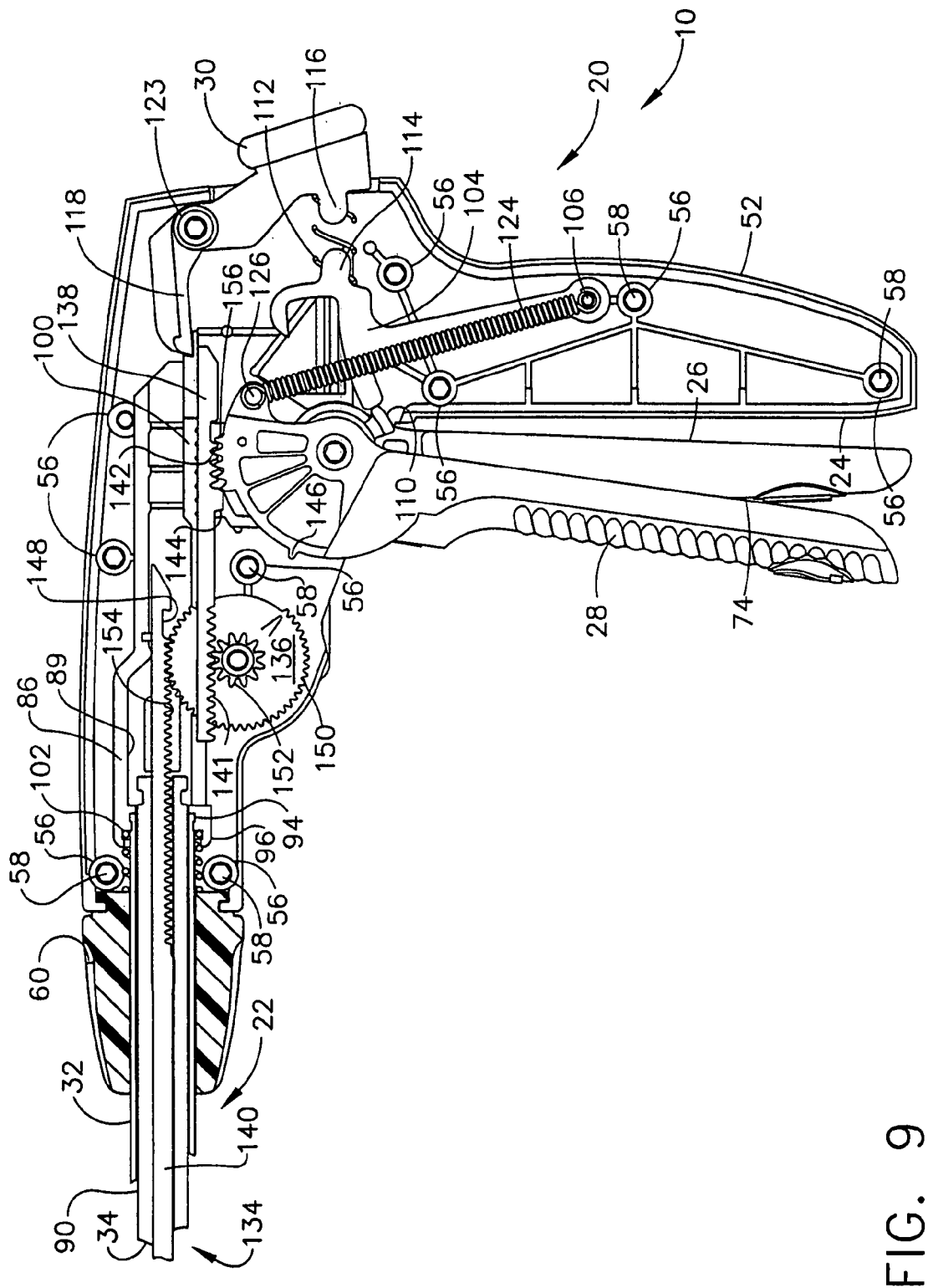
FIG. 9 depicts a side elevational view of the handle portion of the proximal end of the surgical stapling and severing instrument of FIG. 1 with the left side removed to expose interior parts in the stapled and severed ("fired") position.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 30 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied.

It will be appreciated that the handle portion 20 is illustrative and that other actuation mechanisms may be employed. For instance, the closing and firing motions may be generated by automated means.

Separate and Distinct Closing and Firing End Effector

The end effector 12 of the surgical stapling and severing instrument 10 is depicted in further detail in FIGS. 10–16. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
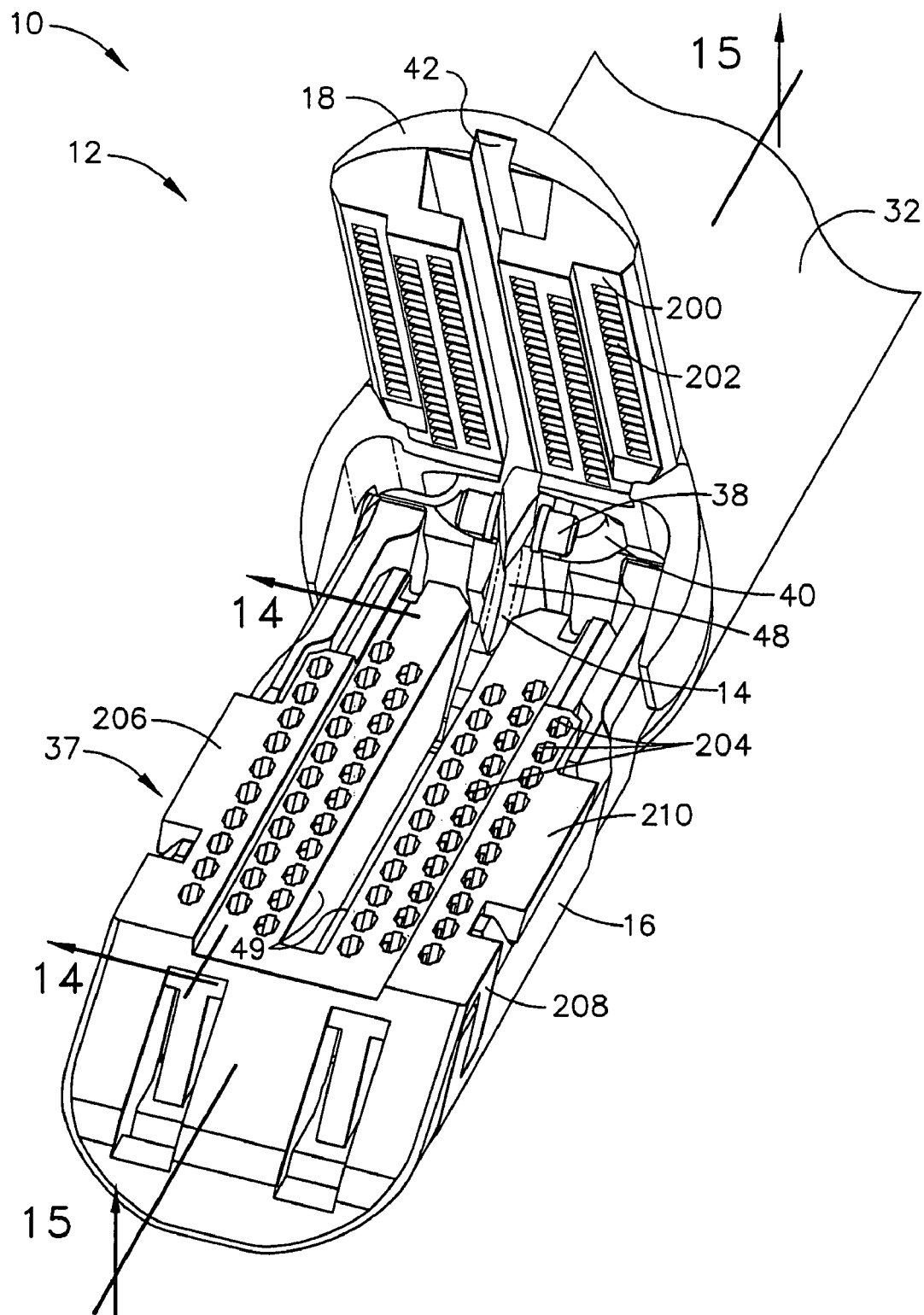
FIG. 10 depicts an isometric view of the end effector at the distal end of the surgical stapling and severing instrument of FIG. 1 with the anvil in the up or open position exposing the staple cartridge and cutting edge of the firing bar.

FIG. 10 depicts the end effector 12, which is in an open position by a retracted closure sleeve 32, with a staple cartridge 37 installed in the staple channel 16. On a lower surface 200 of the anvil 18, a plurality of stapling forming pockets 202 are arrayed to correspond to a plurality of stapler apertures 204 in an upper surface 206 of the staple cartridge 37. The firing bar 14 is at its proximal position, with the upper pin 38 aligned in a noninterfering fashion with the anvil pocket 40. The anvil pocket 40 is shown as communicating with the longitudinal anvil slot 42 in the anvil 18. The distally presented cutting edge 48 of the firing bar 14 is aligned with and proximally removed from the vertical slot 49 in the staple cartridge 37, thereby allowing removal of a spent cartridge 37 and insertion of an unfired cartridge 37, which is snapfit into the staple channel 16. Specifically, extension features 208, 210 of the staple cartridge 37 engage recesses 212, 214 (shown in FIG. 12) of the staple channel 16.

Figure 11:
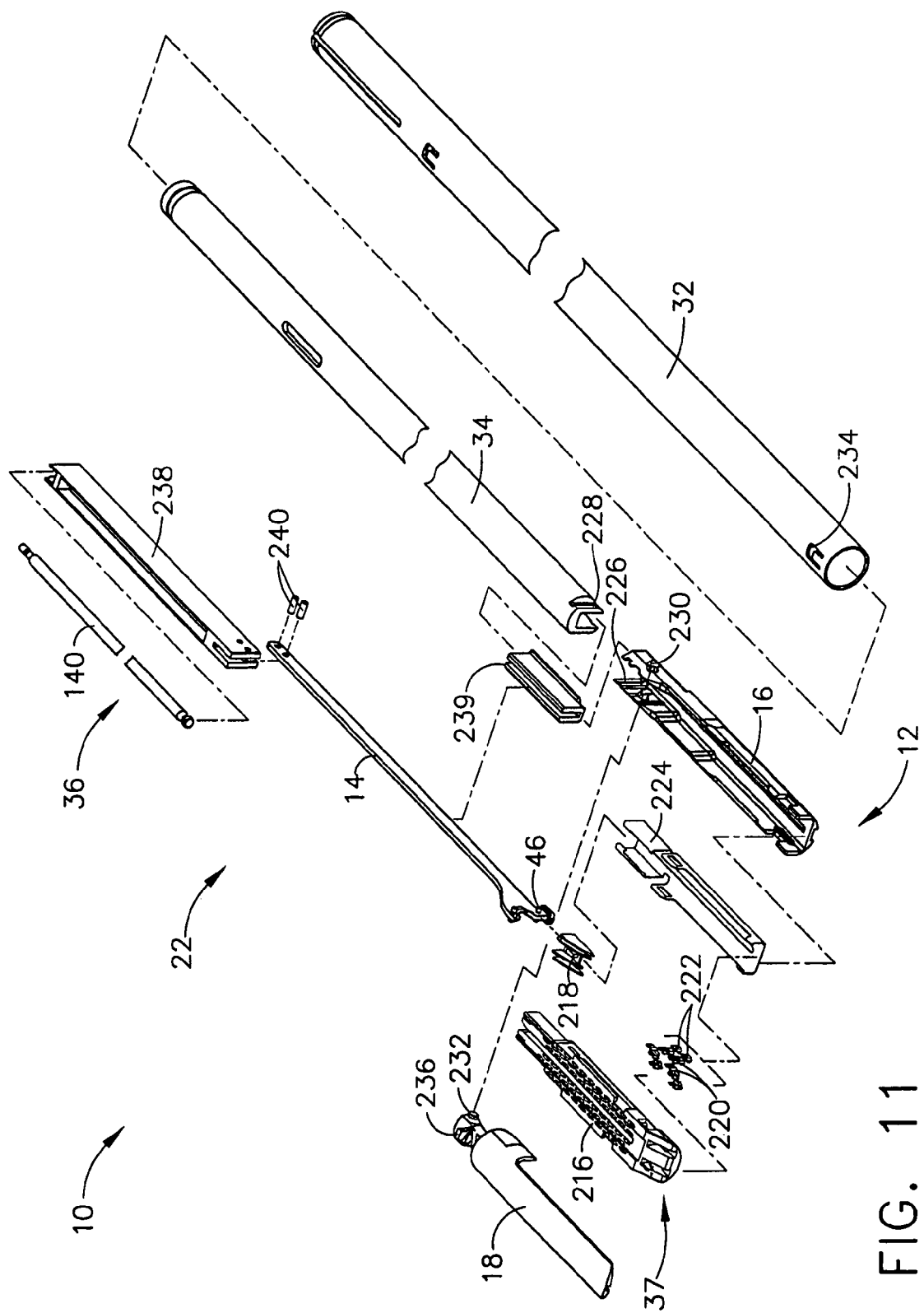
FIG. 11 depicts an isometric, exploded view of the implement portion of the surgical stapling and severing instrument of FIG. 1.

FIG. 11 shows the implement portion 22 of the surgical stapling and severing instrument 10 in disassembled form. The staple cartridge 37 is shown as being comprised of a cartridge body 216, a wedge sled 218, single and double drivers 220, staples 222, and a cartridge tray 224. When assembled, the cartridge tray 224 holds the wedge sled 218, single and double drivers 220, and staples 222 inside the cartridge body 216.

Having a wedge sled 218 integral to the staple cartridge 37 enables a number of flexible design options as compared to incorporating camming surfaces onto a firing bar itself. For instance, a number of different staple cartridges may be selected for use in the instrument 10 with each staple cartridge having a different configuration of rows of staples, each thus having a unique wedge sled configured to contact the middle pin 46 of the firing bar 14 while causing the driving of the staples 222. As another example, the integral wedge sled 218 provides an opportunity for a number of lockout features, described in greater detail in the first and third aforementioned co-pending applications.

The staple channel 16 has a proximally placed attachment cavity 226 that receives a channel anchoring member 228 on the distal end of the frame 34 for attaching the end effector 12 to the handle portion 20. The staple channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 12:
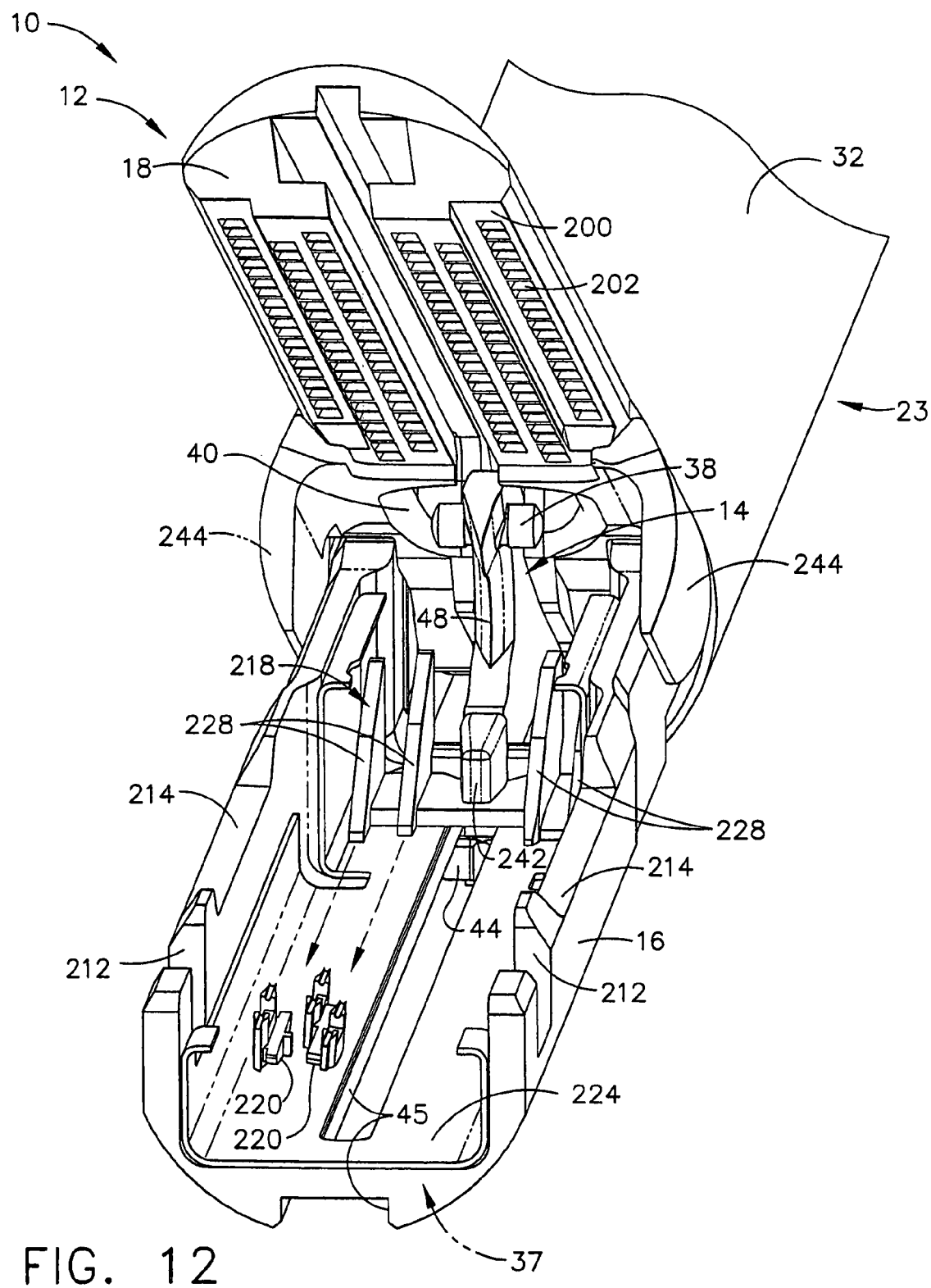
FIG. 12 depicts an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar.

With particular reference to FIG. 12, a portion of the staple cartridge 37 is removed to expose portions of the staple channel 16, such as recesses 212, 214 and to expose some components of the staple cartridge 37 in their unfired position. In particular, the cartridge body 216 (shown in FIG. 11) has been removed. The wedge sled 218 is shown at its proximal, unfired position with a pusher block 242 contacting the middle pin 46 (not shown in FIG. 12) of the firing bar 14. The wedge sled 218 is in longitudinal sliding contact upon the cartridge tray 224 and includes wedges 228 that force upward the single and double drivers 220 as the wedge sled 218 moves distally. Staples 222 (not shown in FIG. 12) resting upon the drivers 220 are thus also forced upward into contact with the anvil forming pockets 202 on the anvil 18 to form closed staples. Also depicted is the channel slot 45 in the staple channel 16 that is aligned with the vertical slot 49 in the staple cartridge 37.

Figure 13:
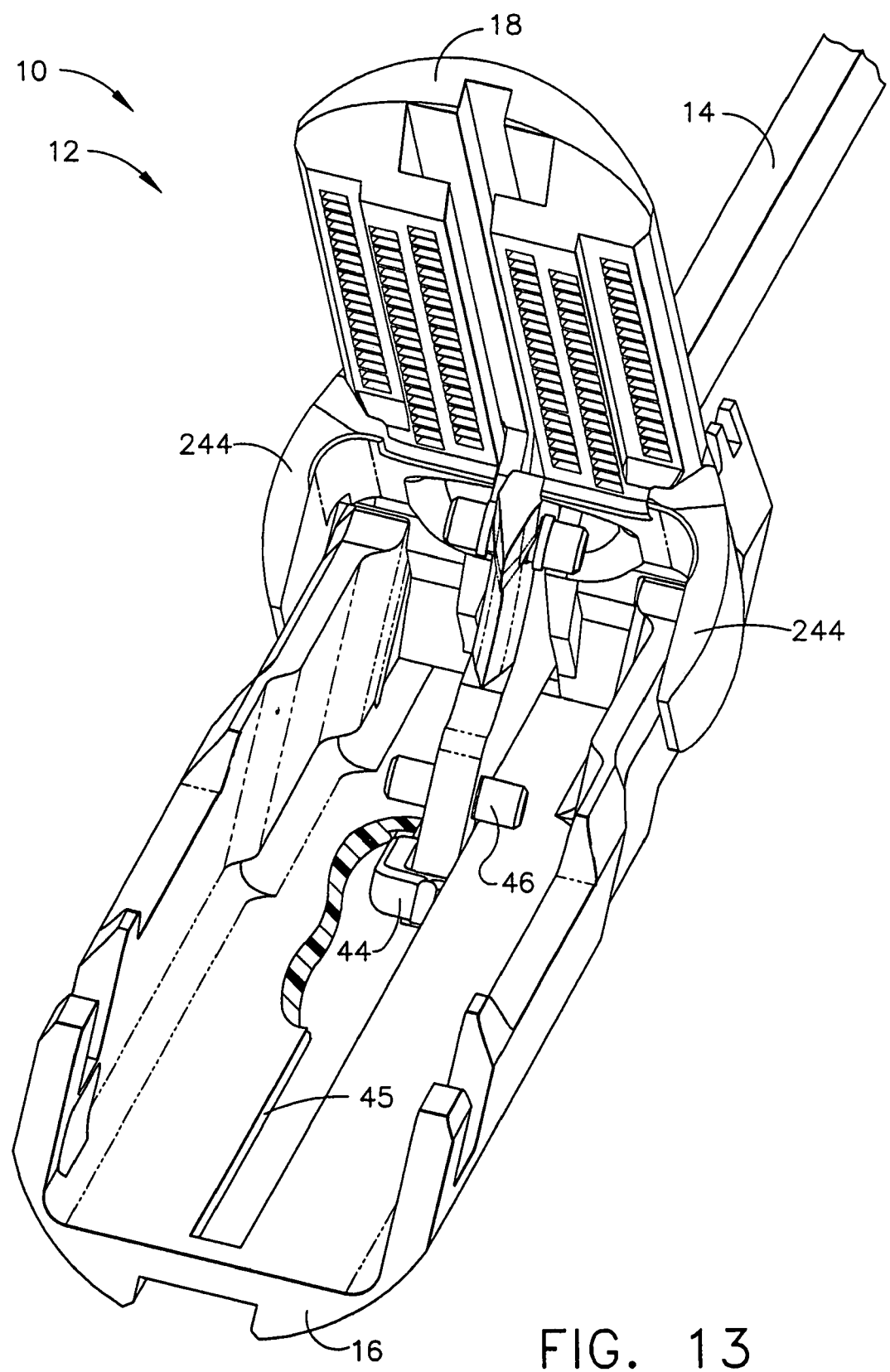
FIG. 13 depicts an isometric view of the distal end of the surgical stapling and severing instrument of FIG. 1 with the anvil in the up or open position with the staple cartridge completely removed and a portion of a staple channel removed to expose a lowermost pin of the firing bar.

FIG. 13 depicts the end effector 12 of FIG. 12 with all of the staple cartridge 37 removed to show the middle pin 46 of the firing bar 14 as well as the portion of the staple channel 16 removed adjacent to the channel slot 45 to expose the firing bar cap 44. In addition, portions of the shaft 23 are removed to expose a proximal portion of the firing bar 14. Projecting downward from the anvil 18 near the pivot, a pair of opposing tissue stops 244 prevent tissue being positioned too far up into the end effector 12 during clamping.

Figure 14:
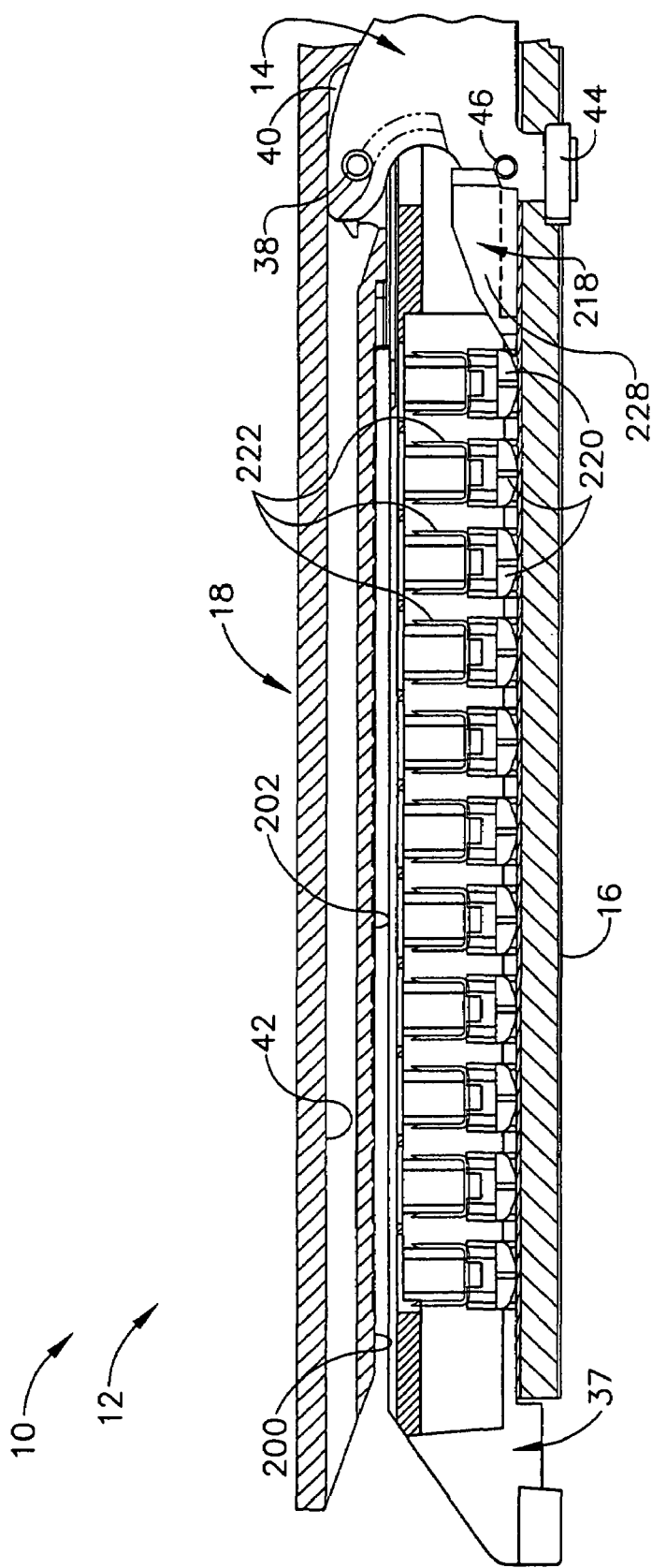
FIG. 14 depicts a side elevation view in section showing a mechanical relationship between the anvil, staple channel, and staple cartridge in the closed position of the surgical stapling and severing instrument of FIG. 1, the section generally taken along lines 14—14 of FIG. 10 to expose wedge sled, staple drivers and staples but also depicting the firing bar along the longitudinal centerline.

FIG. 14 depicts the end effector 12 closed in a tissue clamping position with the firing bar 14 unfired. The upper pin 38 is in the anvil pocket 40, vertically aligned with the anvil slot 42 for distal longitudinal movement of the firing bar 14 during firing. The middle pin 46 is positioned to push the wedge sled 218 distally so that wedge 228 sequentially contacts and lifts double drivers 220 and the respective staples 222 into forming contact with staple forming pockets 202 in the lower surface 200 of the anvil 18.

Figure 15:
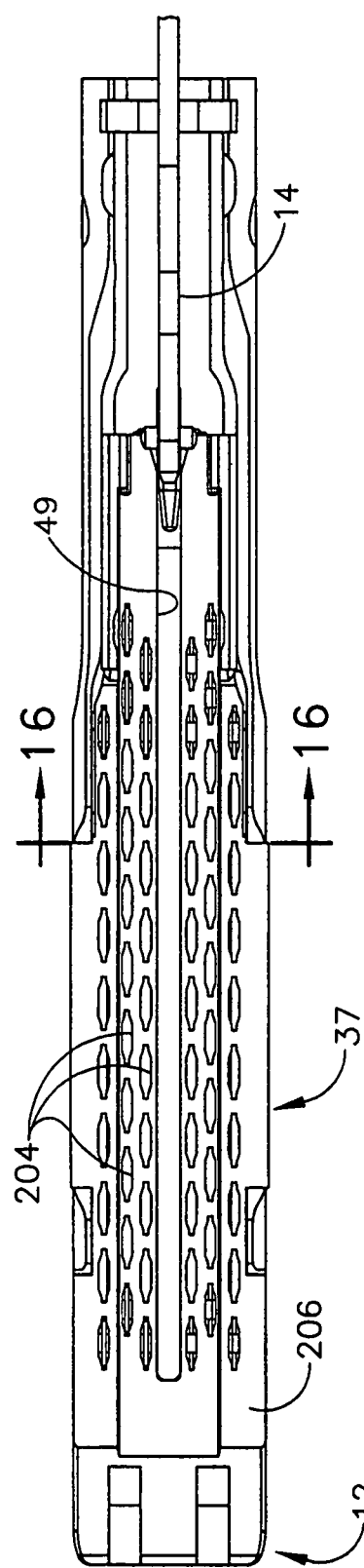
FIG. 15 depicts a section view of the end effector of the surgical stapling and severing instrument with the cartridge and firing bar in the start position taken along line 15—15 of FIG. 10.

FIG. 15 depicts the upper surface 206 of the staple cartridge 37 with the firing bar 14 in its unfired, proximal position. The stapler apertures 204 are arrayed on each side of the vertical slot 49 in the staple cartridge 37.

Figure 16:
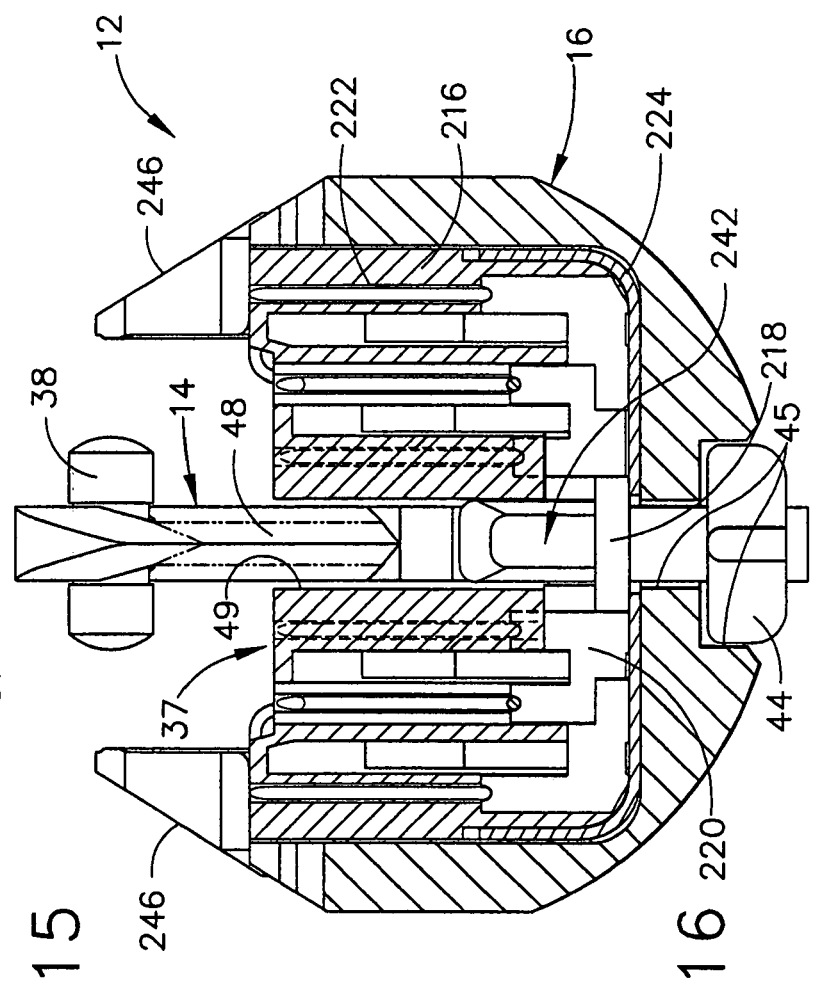
FIG. 16 depicts a section view taken along line 16—16 of FIG. 15 showing the cross-sectional relationship between the firing bar, staple channel, wedge sled, staple drivers, staples and staple cartridge.

FIG. 16 depicts the end effector 12 near the pivot showing that the staple channel 16 has opposing ramp portions 246 to thereby cooperate with the tissue stops 244 of the anvil 18 (not shown in FIG. 16) to prevent tissue from jamming the end effector 12. Also depicted in greater detail are the double drivers 220 and their relation to the staples 222.

Operation.

Figure 17:
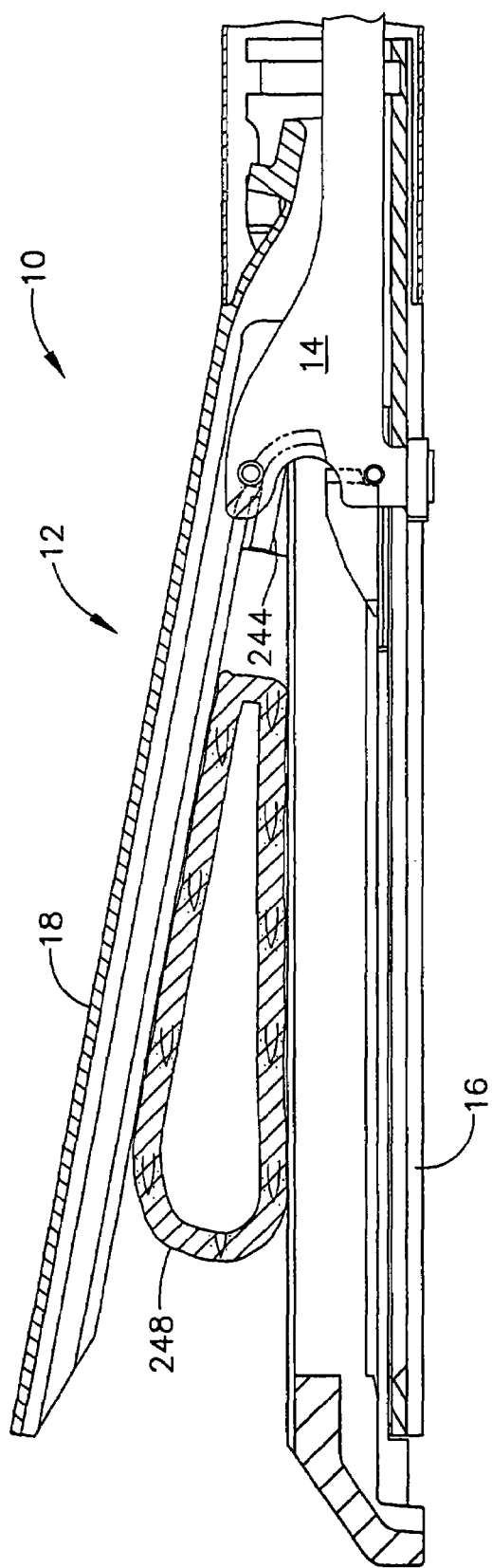
FIG. 17 depicts a side elevation section view of the surgical stapling and severing instrument of FIG. 1 taken along the longitudinal centerline of the end effector in a partially closed but unclamped position gripping tissue.

In use, the surgical stapling and severing instrument 10 is used as depicted in FIGS. 1, 2, and 17–23. In FIGS. 1–2, the instrument 10 is in its start position, having had an unfired, fully loaded staple cartridge 37 snap-fitted into the distal end of the staple channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 37 and the anvil 18, as depicted in FIG. 17.

Figure 18:
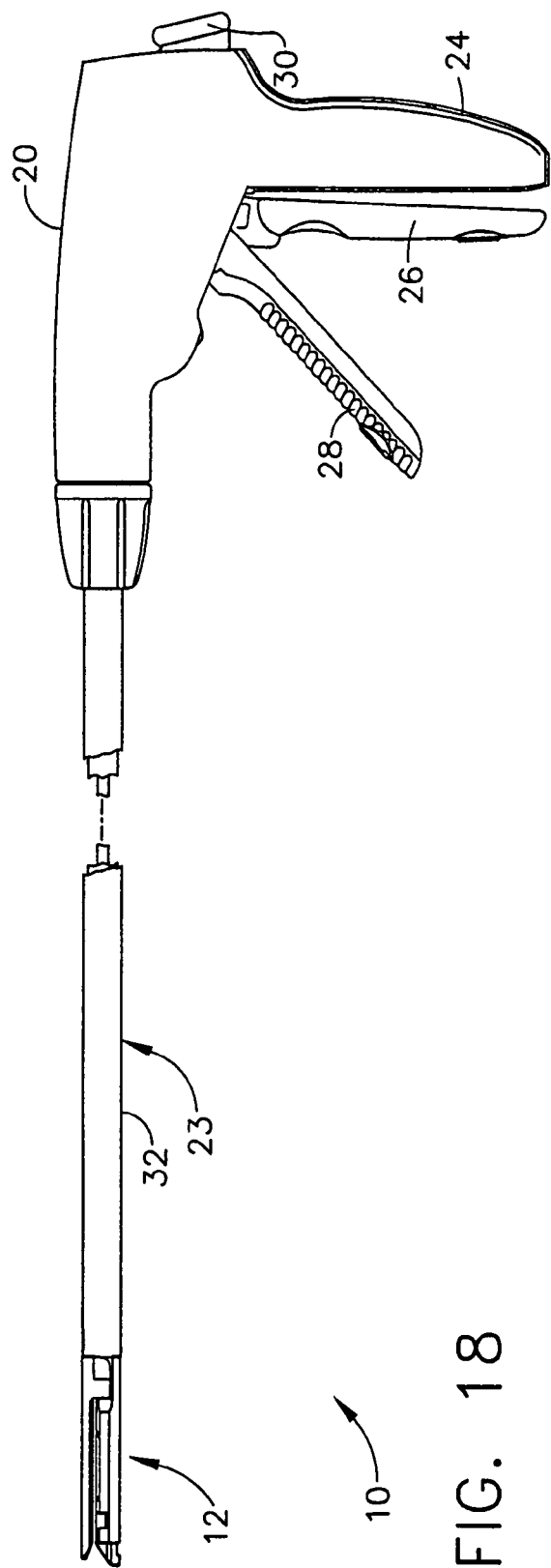
FIG. 18 depicts a partially cutaway side elevational view of the surgical stapling and severing instrument of FIG. 1 in the closed or clamped position.
Figure 19:
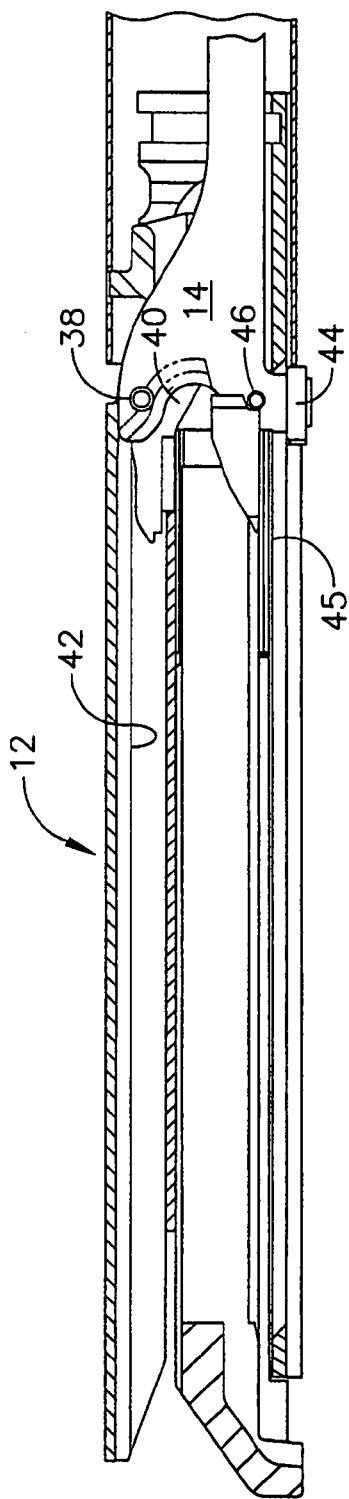
FIG. 19 depicts a side elevation view in centerline section of the distal end of the surgical stapling and severing instrument of FIG. 1 in the closed or clamped position with tissue properly compressed.

With reference to FIGS. 18–19, next, the clinician moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the staple channel 16 affirmatively engaged about the channel slot 45 by the middle pin 46 and the firing bar cap 44.

Figure 20:
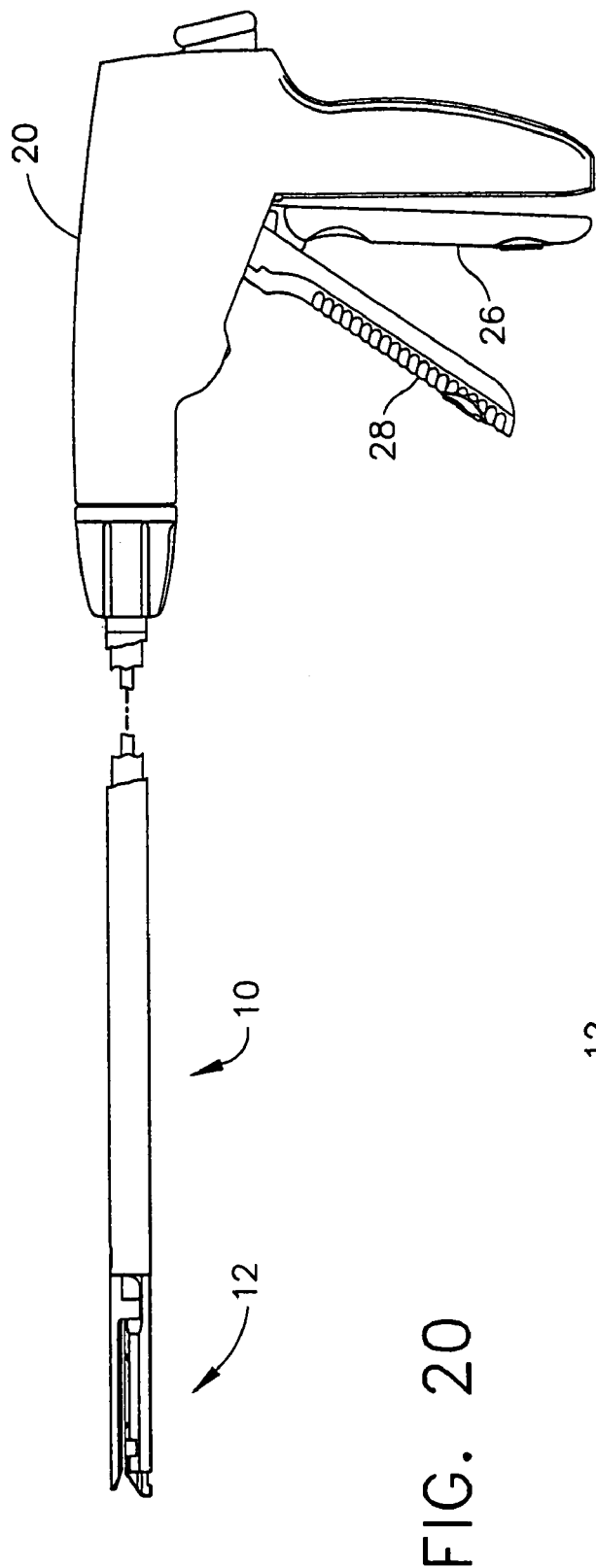
FIG. 20 depicts a partially cutaway side elevation view of the surgical stapling and severing instrument of FIG. 1 in a partially fired position.
Figure 21:
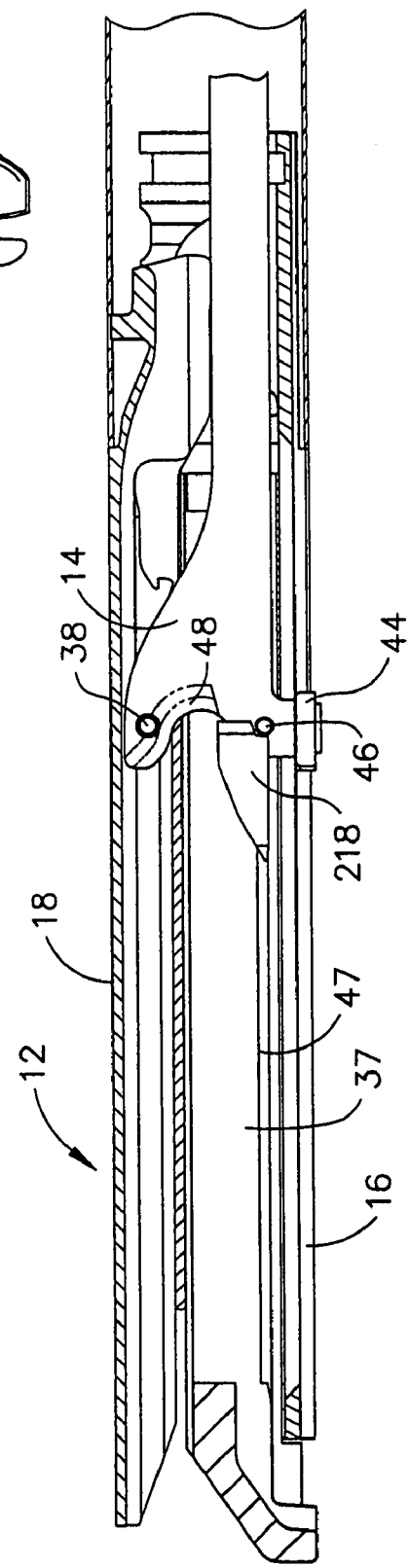
FIG. 21 depicts a view in centerline section of the distal end of the surgical stapling and severing instrument of FIG. 1 in a partially fired position.

With reference to FIGS. 20–21, after tissue clamping has occurred, the clinician moves the firing trigger 28 proximally causing the firing bar 14 to move distally into the end effector 12. In particular, the middle pin 46 enters the staple cartridge 37 through the firing drive slot 47 to effect the firing of the staples 222 (not shown in FIGS. 20–21) via wedge sled 218 toward the anvil 18. The lower most pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the staple channel 16 throughout its distal firing movement.

With reference to FIGS. 22–23, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is completed by releasing the firing trigger 28 and then depressing the release button 30 while simultaneously squeezing the closure trigger 26 to open the end effector 12.

Single Lockout for Missing/Spent Staple Cartridge

Figure 24:
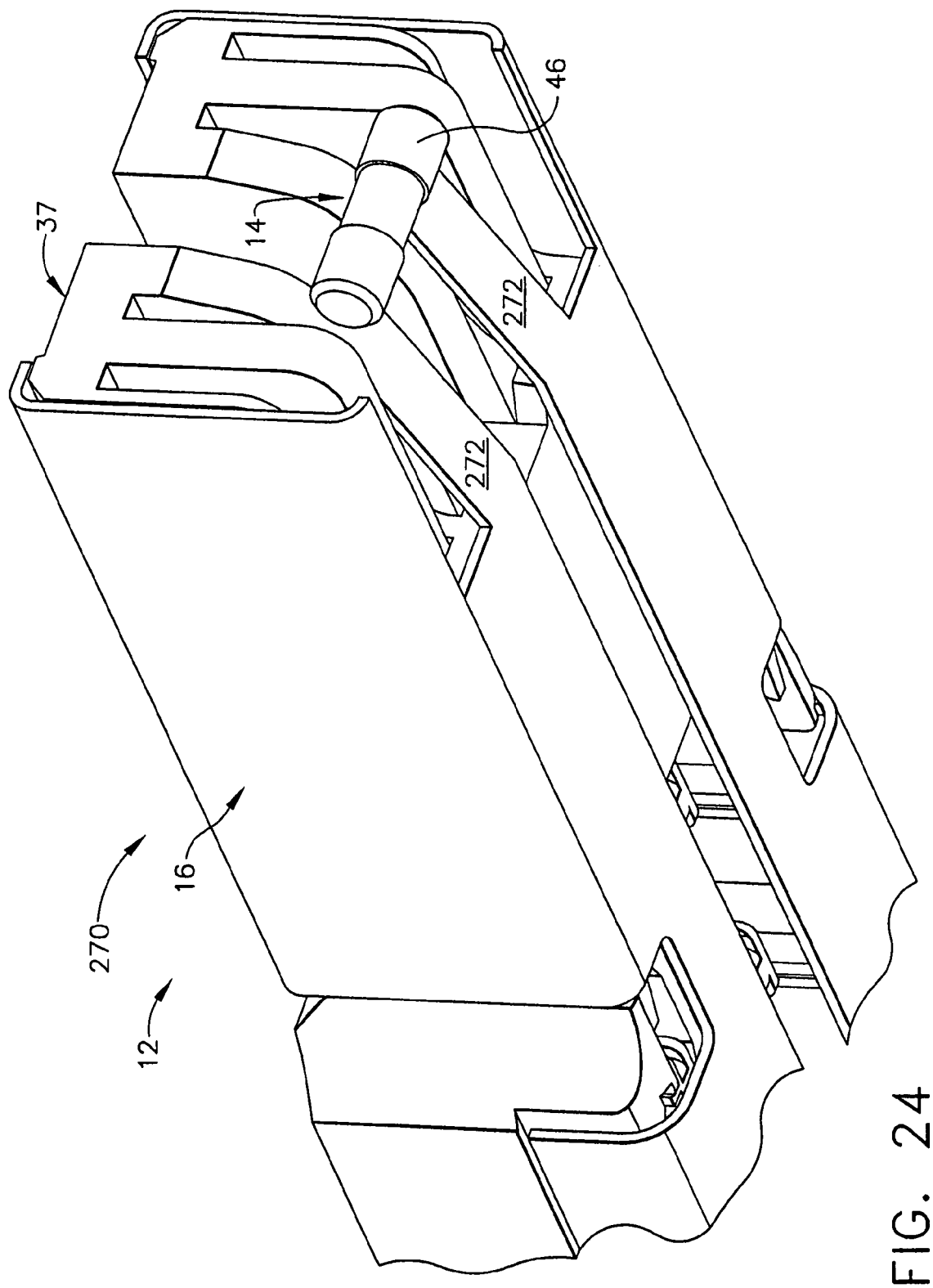
FIG. 24 depicts a perspective view looking distally at the staple channel of FIG. 1 partially cut away to expose a cartridge body and a single lockout mechanism engaging a middle pin of a firing bar.

As described above, the E-beam firing bar 14 provides unique capabilities for affirmatively spacing the end effector 12 while simultaneously severing tissue and effecting the forming of staples on each side of the cut. With reference to FIG. 24, preventing the distal movement of the firing bar 14 thus prevents the inadvertent severing of tissue. A single lockout mechanism 270 advantageously responds to a missing staple cartridge 37 or a spent staple cartridge 37, the latter condition depicted in FIG. 24, by blocking the middle pin 46 of the firing bar (only the middle pin of the firing bar being shown in FIG. 24).

In particular, the single lockout mechanism 270 is depicted as a pair of bent spring fingers 272 positioned in the staple channel 16 to respond to both conditions: missing cartridge and spent cartridge. In particular, the bent spring fingers 272 raise up to block the middle pin 46 of the firing bar 14 when the wedge sled 218 (not shown in FIG. 24) is not present, such as when the cartridge 37 is removed or when the cartridge 37 has been fired.

Figure 25:
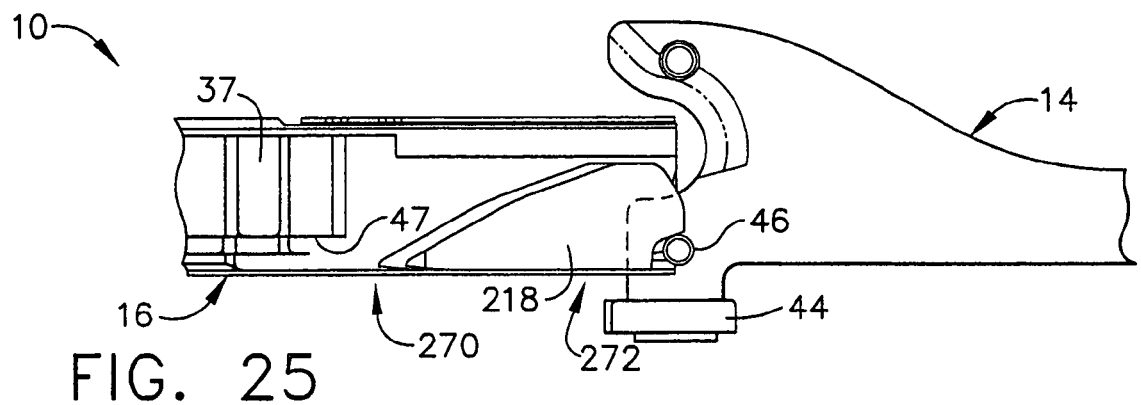
FIGS. 25–28 depict a cross-sectional side detail view of the single lockout mechanism, staple cartridge and firing bar of FIG. 24, sequentially shown in a cartridge loaded and unfired state in FIG. 25, a cartridge being fired state in FIG. 26, a spent cartridge with firing bar being retracted state in FIG. 27, and spent cartridge with firing bar retracted state in FIG. 28.

FIGS. 25–28 depict the single lockout mechanism 270, specifically the bent sprint fingers 272 sequentially as the surgical stapling and severing instrument 10 is fired. In FIG. 25, an unfired staple cartridge 37 has been inserted into the staple channel 16 with the wedge sled 218 depressing the bent spring fingers 272 so that the firing drive slot 47 formed between the cartridge 37 and the staple channel 16 is unimpeded.

Figure 26:
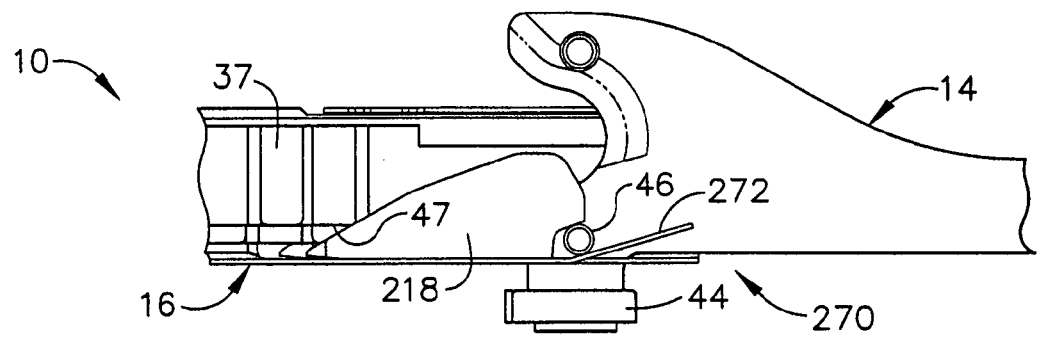

In FIG. 26, firing of the cartridge 37 has commenced, with the wedge sled 218 and the middle pin 46 of the firing bar 14 having distally traversed off of the bent spring fingers 272, which then spring up into the firing drive slot 47.

Figure 27:
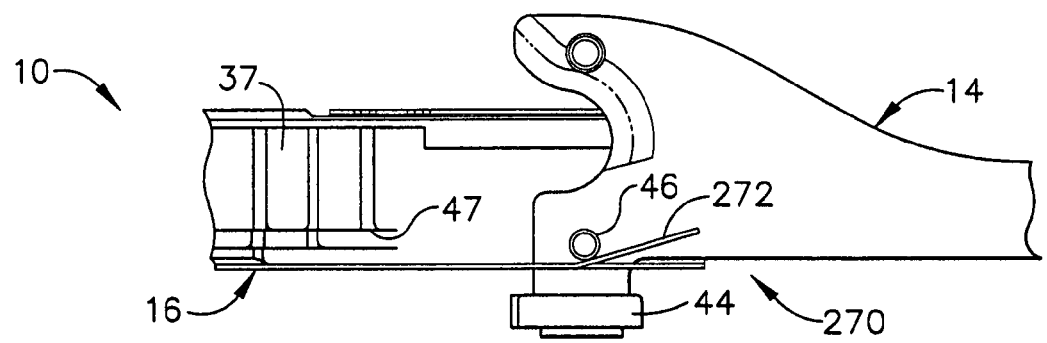

In FIG. 27, the staple cartridge 37 is now spent with the wedge sled 218 fully driven distally and no longer depicted.

The firing bar 14 is being retracted proximally. Since the bent spring fingers 272 pivot from a more distal point, the firing bar 14 is able to ride up onto the bent spring fingers 272 during retraction, causing them to be depressed out of the firing drive slot 47.

Figure 28:
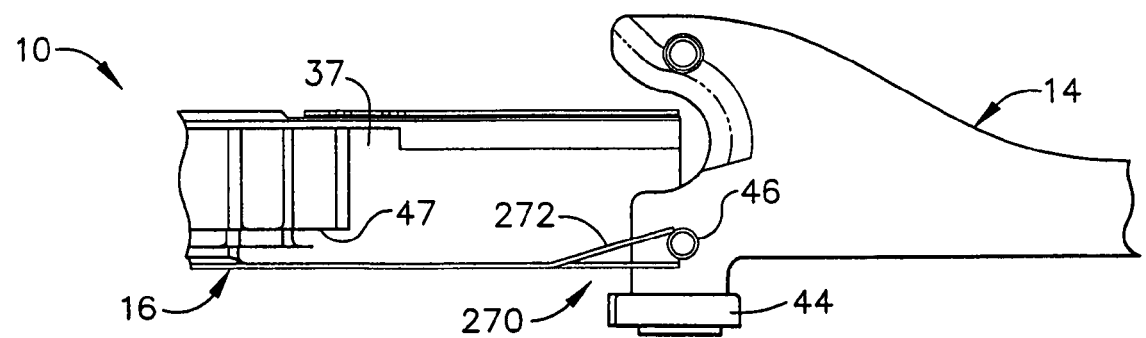

In FIG. 28, the firing bar 14 is fully retracted and now confronts a non-depressed pair of bent spring fingers 272 to prevent distal movement. The single lockout mechanism 270 thereby remains activated during the period in which the spent staple cartridge 37 is removed until an unfired staple cartridge 37 is installed.

Figure 29:
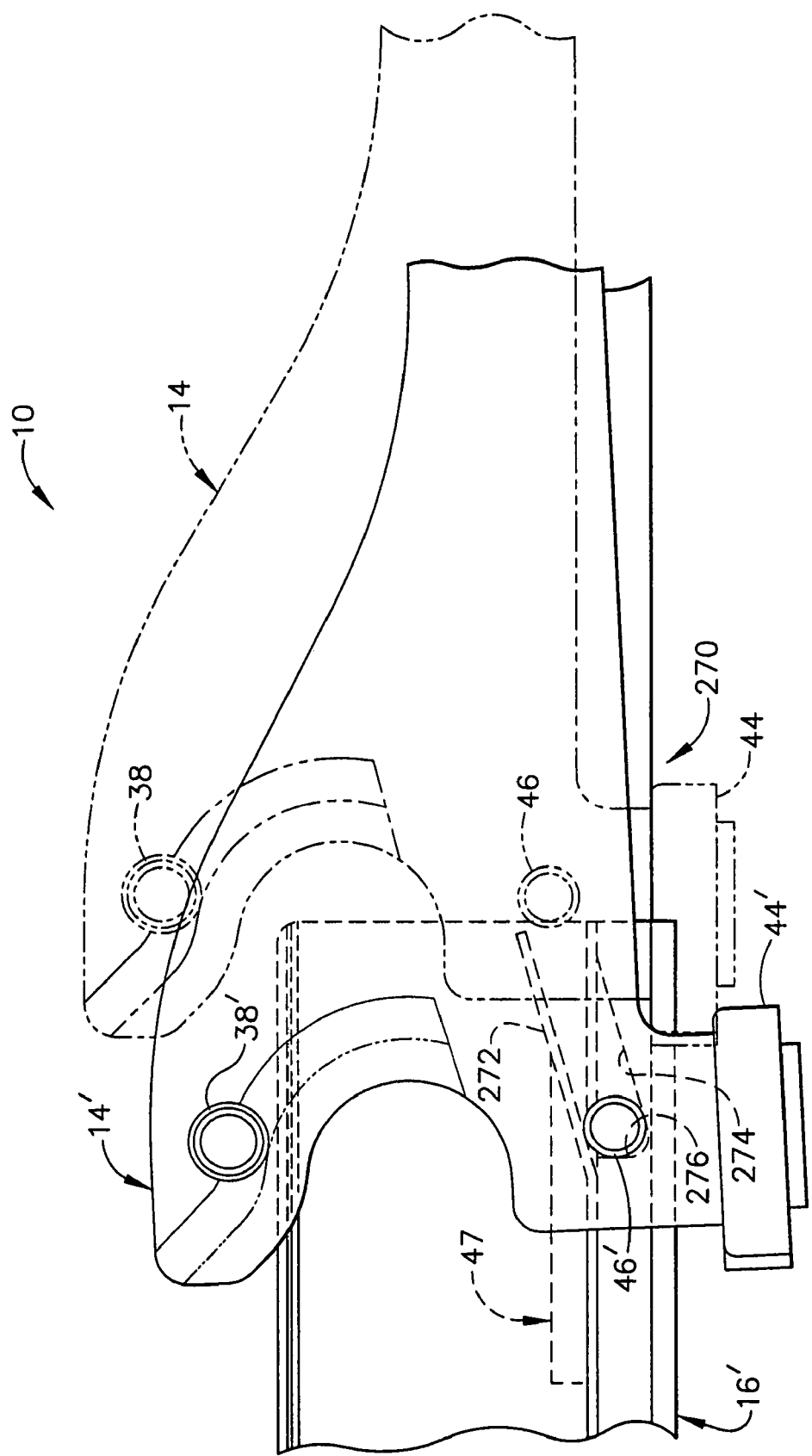
FIG. 29 depicts the single lockout mechanism of FIG. 24 further incorporating a lockout trough.

FIG. 29 depicts a lockout trough 274 that may advantageously be included in the single lockout mechanism 270 in order to provide increased mechanical strength. In some applications, it may be desirable to block strong firing motions without damage to the bent spring fingers 272. The lockout trough 274 communicates with the firing drive slot 47 when the bent spring fingers 272 are not depressed. Moreover, the lockout trough 274 is downwardly ramped in a distal direction such that the middle pin 46 of the firing bar 14 is directed toward an abutting surface 276 at a distal end of the lockout trough 274, thereby reacting the distal movement of the firing bar 14 into a staple channel 16'. In particular, the firing bar 14 in its initial position moves to a distal and lowered position, depicted at 14', wherein the middle pin 46 moves to a position depicted as 46'. It will be appreciated that the upper pin 38 and lower firing bar cap 44, as each moves to distal and lowered positions 38' and 44' respectively, position the middle pin 46 against staple channel 16 so that the middle pin 46 enters the lockout trough 274.

It will be further appreciated that the firing bar 14' may be readily retracted from the lockout trough 274. Moreover, insofar as the upper pin 38' would be engaging the anvil 18 (not shown in FIG. 29) in this position, the clinician would have to retract the firing bar 14' so that the anvil 18 could be opened in order to insert an unfired staple cartridge 37, and thus the firing bar 14 would be fully retracted and would not impede the depressing of the bent spring fingers 272 to their inactivated position.

Figure 30:
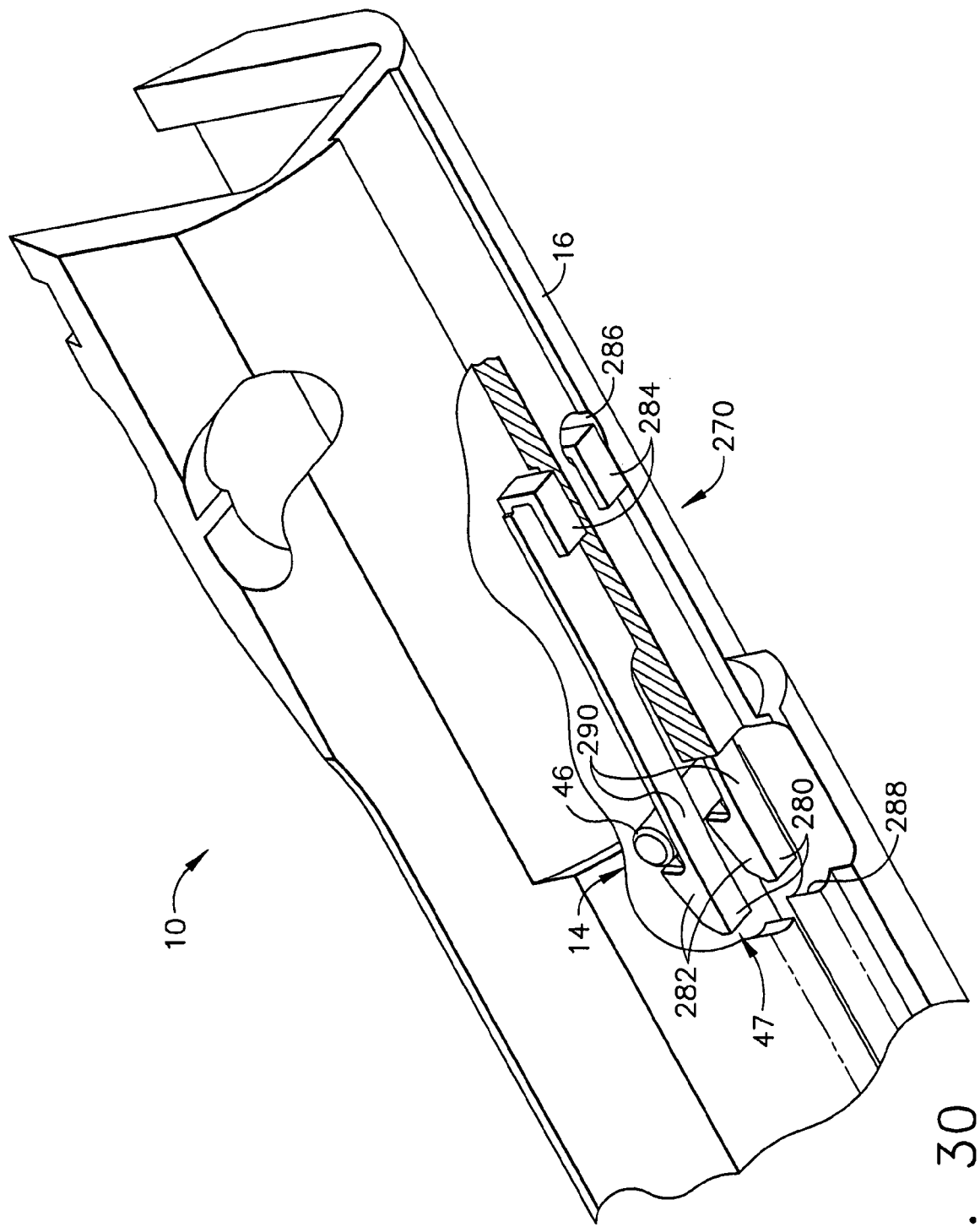
FIG. 30 depicts a bottom perspective view of a staple channel of FIG. 1 partially cut away to show another single lockout mechanism engaging the middle pin of a firing bar when a staple cartridge is missing.

FIG. 30 depicts another single lockout mechanism 270, depicted as a pair of lockout hooks 280 having ramped ends 282 distally placed with regard to attachment devices 284 inserted through apertures 286 in the staple channel 16. The ramped ends 282 lie above a hook recess 288 defined in the staple channel 16. Thus, when each ramped end 282 is contacted by a wedge sled 218 of an unfired staple cartridge 37 (not shown in FIG. 30), the ramped ends 282 are depressed into the hook recess 288, thereby clearing the way for the middle pin 46 of the firing bar 14 (only the middle pin shown in FIG. 30) to move distally to fire the staple cartridge 37. A thin shaft 290 coupling the attachment devices 284 respectively to the ramped end 282 of each lockout hook 280 resiliently responds to the absence of a wedge sled 218, as depicted, wherein the ramped ends 282 return to impede the firing drive slot 47 to block a retracted middle pin 46 of the firing bar.

Figure 31:
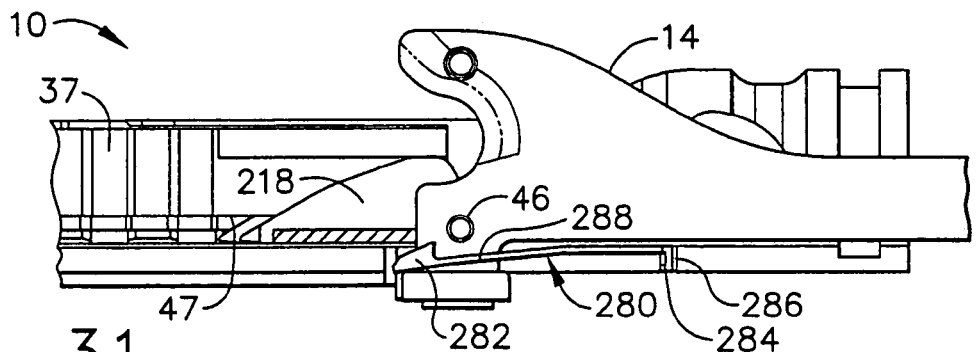
FIGS. 31–34 depict a cross-sectional side detail view of the single lockout mechanism of FIG. 30, sequentially shown in a cartridge loaded and unfired state in FIG. 31, a cartridge being fired state in FIG. 32, a spent cartridge with firing bar being retracted state in FIG. 33, and a spent-cartridge-with-firing-bar-retracted state in FIG. 34.
Figure 32:
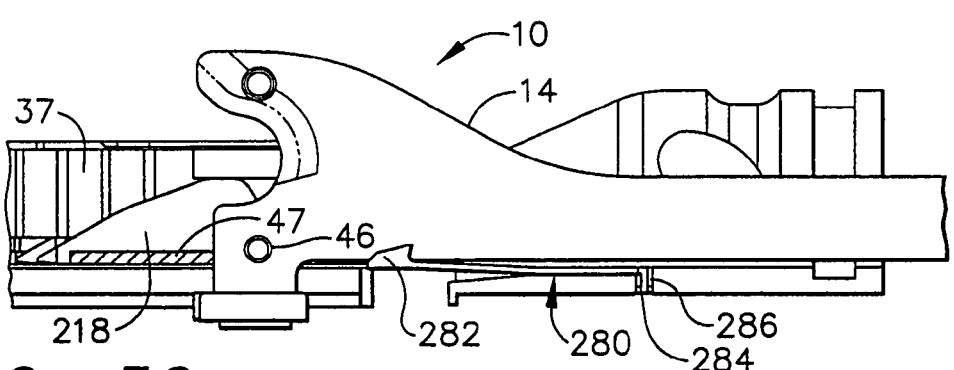

FIGS. 31–34 depict the sequence of operation of the lockout hooks 280. In FIG. 31, the staple cartridge 37 is unfired so that the distally positioned wedge sled 218 depresses the ramped ends 282 into the hook recess 288, allowing the middle pin 46 of the firing bar 14 to move distally during firing, as depicted in FIG. 32. With the wedge sled 218 and middle pin 46 distally removed with respect to the lockout mechanism 270, the ramped ends 282 resiliently raise out of the hook recess 282 to occupy the firing drive slot 47.

Figure 33:
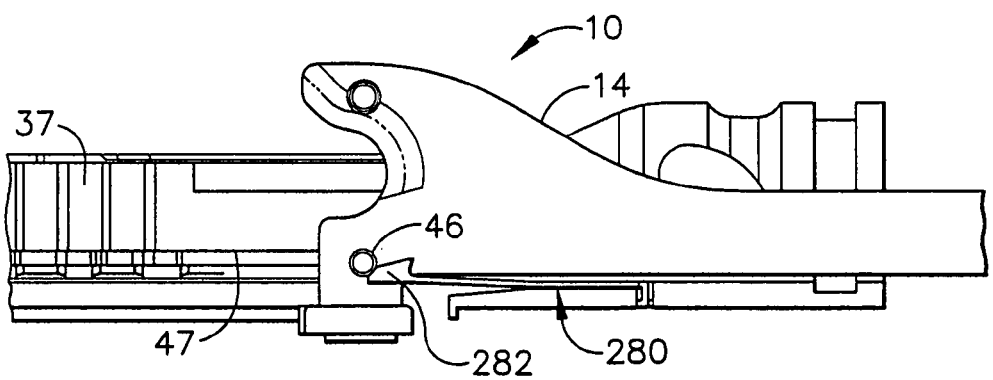
Figure 34:
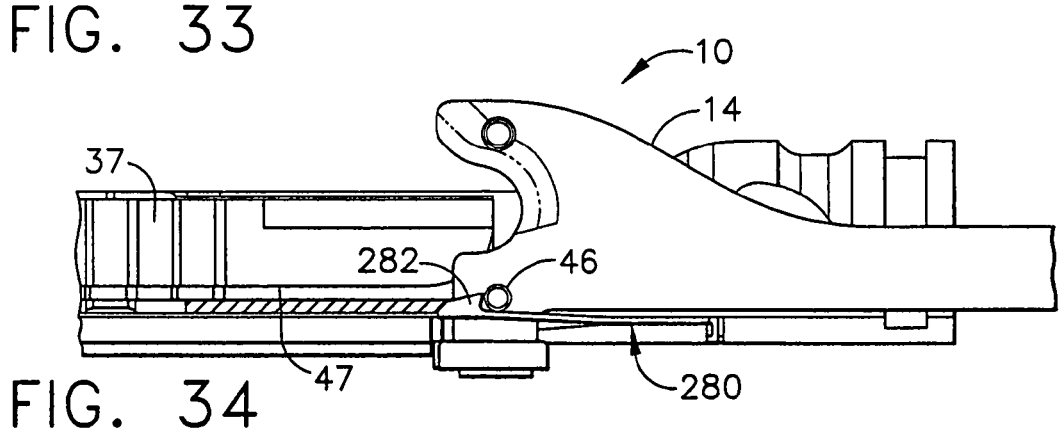

In FIG. 33, the firing bar 14 is being retracted to the point of contacting the ramped ends 282 of the lockout hook 280. Since the distal end of the ramped ends 282 is lower than the proximal part of the ramped ends 282, the middle pin 46 of the firing bar 14 rides over the ramped ends 282, forcing them down into the hook recess 288 until middle pin 46 is past the ramped ends 282, as depicted in FIG. 34, wherein the ramped ends 282 resiliently spring back up to block the middle pin 46. Thus, the firing bar 14 is prevented from distal movement while the spent staple cartridge 37 is replaced with an unfired staple cartridge 37.

Electroactive Polymers.

Electroactive polymers (EAPs) are a set of conductive doped polymers that change shape when electrical voltage is applied. In essence, the conductive polymer is paired to some form of ionic fluid or gel and electrodes. Flow of the ions from the fluid/gel into or out of the conductive polymer is induced by the voltage potential applied and this flow induces the shape change of the polymer. The voltage potential ranges from 1V to 4 kV, depending on the polymer and ionic fluid used. Some of the EAPs contract when voltage is applied and some expand. The EAPs may be paired to mechanical means such as springs or flexible plates to change the effect that is caused when the voltage is applied.

There are two basic types of EAPs and multiple configurations of each type. The two basic types are a fiber bundle and a laminate version. The fiber bundle consists of fibers around 30–50 microns. These fibers may be woven into a bundle much like textiles and are often called EAP yarn because of this. This type of EAP contracts when voltage is applied. The electrodes are usually made up of a central wire core and a conductive outer sheath that also serves to contain the ionic fluid that surrounds the fiber bundles. An example of a commercially available fiber EAP material is manufactured by Santa Fe Science and Technology and sold as PANION™ fiber and is described in U.S. Pat. No. 6,667,825, which is hereby incorporated by reference in its entirety.

The other type is a laminate structure, which consists of a layer of EAP polymer, a layer of ionic gel and two flexible plates that are attached to either side of the laminate. When a voltage is applied, the square laminate plate expands in one direction and contracts in the perpendicular direction. An example of a commercially available laminate (plate) EAP material is from Artificial Muscle Inc, a division of SRI Laboratories. Plate EAP material is also available from EAMEX of Japan and is referred to as thin film EAP.

It should be noted that EAPs do not change volume when energized; they merely expand or contract in one direction while doing the opposite in the transverse direction. The laminate version may be used in its basic form by containing one side against a rigid structure and using the other much like a piston. The laminate version may also be adhered to either side of a flexible plate. When one side of the flexible plate EAP is energized, it expands flexing the plate in the opposite direction. This allows the plate to be flexed in either direction, depending on which side is energized.

An EAP actuator usually consists of numerous layers or fibers bundled together to work in cooperation. The mechanical configuration of the EAP determines the EAP actuator and its capabilities for motion. The EAP may be formed into long stands and wrapped around a single central electrode. A flexible exterior outer sleeve will form the other electrode for the actuator as well as contain the ionic fluid necessary for the function of the device. In this configuration when the electrical field is applied to the electrodes, the strands of EAP shorten. This configuration of EAP actuator is called a fiber EAP actuator. Likewise, the laminate configuration may be placed in numerous layers on either side of a flexible plate or merely in layers on itself to increase its capabilities. Typical fiber structures have an effective strain of 2–4% where the typical laminate version achieves 20–30%, utilizing much higher voltages.

For instance, a laminate EAP composite may be formed from a positive plate electrode layer attached to an EAP layer, which in turn is attached to an ionic cell layer, which in turn is attached to a negative plate electrode layer. A plurality of laminate EAP composites may be affixed in a stack by adhesive layers therebetween to form an EAP plate actuator. It should be appreciated that opposing EAP actuators may be formed that can selectively bend in either direction.

A contracting EAP fiber actuator may include a longitudinal platinum cathode wire that passes through an insulative polymer proximal end cap through an elongate cylindrical cavity formed within a plastic cylinder wall that is conductively doped to serve as a positive anode. A distal end of the platinum cathode wire is embedded into an insulative polymer distal end cap. A plurality of contracting polymer fibers are arranged parallel with and surrounding the cathode wire and have their ends embedded into respective end caps. The plastic cylinder wall is peripherally attached around respective end caps to enclose the cylindrical cavity to seal in ionic fluid or gel that fills the space between contracting polymer fibers and cathode wire. When a voltage is applied across the plastic cylinder wall (anode) and cathode wire, ionic fluid enters the contracting polymer fibers, causing their outer diameter to swell with a corresponding contraction in length, thereby drawing the end caps toward one another.

Two-Piece Knife with Vertically Expanded EAP Lockout Mechanism.

In FIG. 1, a surgical stapling and severing instrument 510 is shown open, with an E-beam 512 fully retracted within a staple applying assembly 514. During assembly, a lower foot 516 of the E-beam 512 is dropped through a widened hole 518 in a staple channel 520 of the staple applying assembly 514. The E-beam 512 is then advanced such that the E-beam 512 slides distally along a lower track 522 formed in the staple channel 520. In particular, the lower track 522 includes a narrow slot 524 that opens up as a widened slot 526 on an undersurface of the staple channel 520 to form an inverted T-shape in lateral cross-section that communicates with the widened hole 518. Once assembled, the components proximally coupled to a firing bar 528, which is attached to the E-beam 512, do not allow the lower foot 516 to proximally travel again to the widened hole 518 to permit disengagement.

Figure 35:
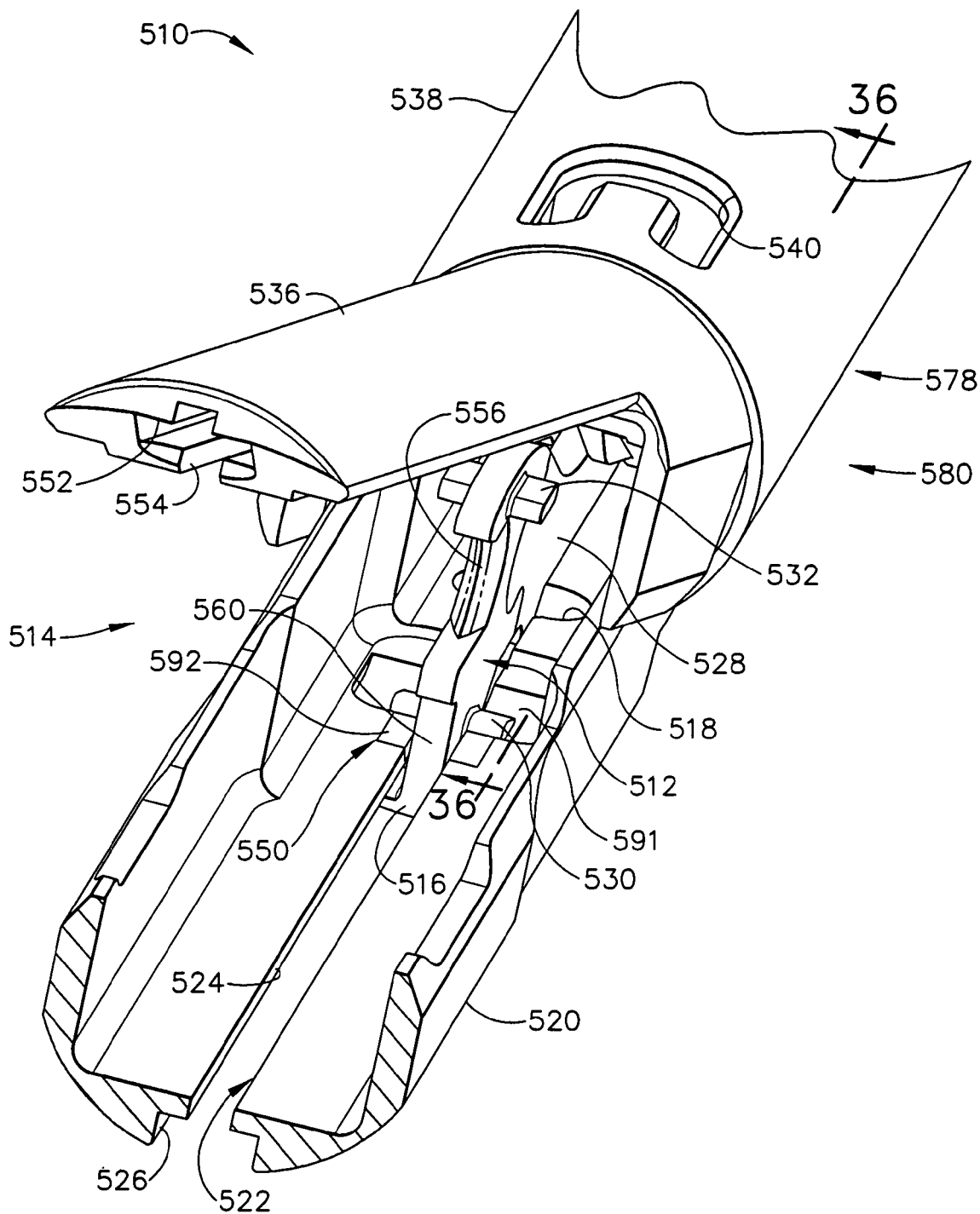
FIG. 35 is a front perspective, partially cutaway view of an alternative implement portion for a surgical severing and stapling instrument, which has a staple cartridge removed, that incorporates an electroactive polymer (EAP) actuated lockout mechanism.
Figure 36:
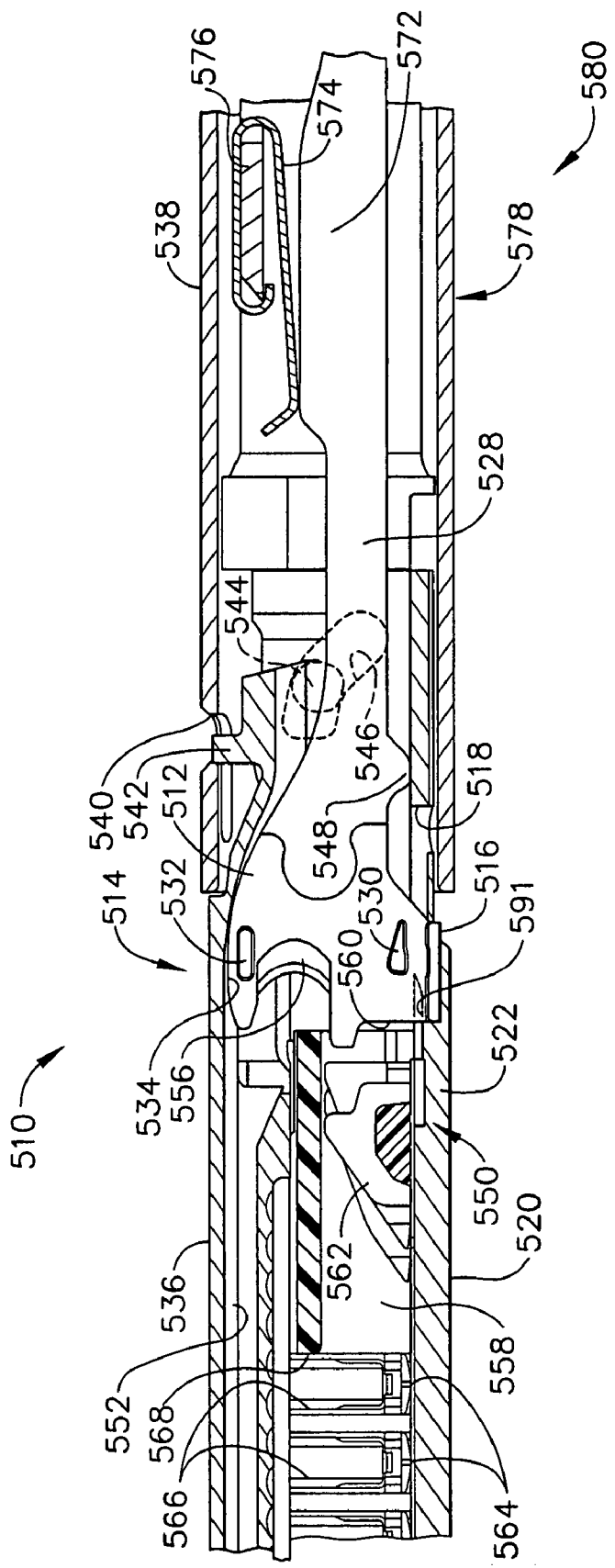
FIG. 36 is a left side view in elevation of the alternative implement portion, which now includes an unfired staple cartridge, taken in cross-section along lines 36—36 of FIG. 35 through the EAP actuated lockout mechanism that is in a deactivated state and depicting an E-beam/firing bar in a retracted condition proximal to an unspent staple cartridge.

With reference to FIGS. 35–36, middle pin 530 of the E-beam 512 slide along a top surface of the staple cartridge 520 to each side of the lower track 522, cooperating with the lower foot 516 to longitudinally and slidingly engage the staple channel 520. Upper pins 532 of the E-beam 512 reside within an anvil pocket 534 (FIG. 36) when proximally retracted, allowing repeated opening and closing of an upperjaw, or anvil, 536 of the staple applying assembly 514 in response to a closure motion of a closure sleeve assembly 538 engaged at a horseshoe-shaped aperture 540 to a closure feature 542 of the anvil 536. The anvil 536 pivots about proximal anvil pivot pins 544 that slide within a respective anvil pivot recess 546 in the staple channel 520 (shown in phantom in FIG. 36).

In FIG. 36, the proximal firing bar 528 of the E-beam 512 includes a downward projection 548 that slides against the staple channel 520, advantageously raising the distal E-beam 512 when retracted, advantageously preparing the staple applying assembly 514 for insertion through a trocar for instance and staging the middle pins 530 for entering an EAP acuated lockout mechanism 550.

Figure 37:
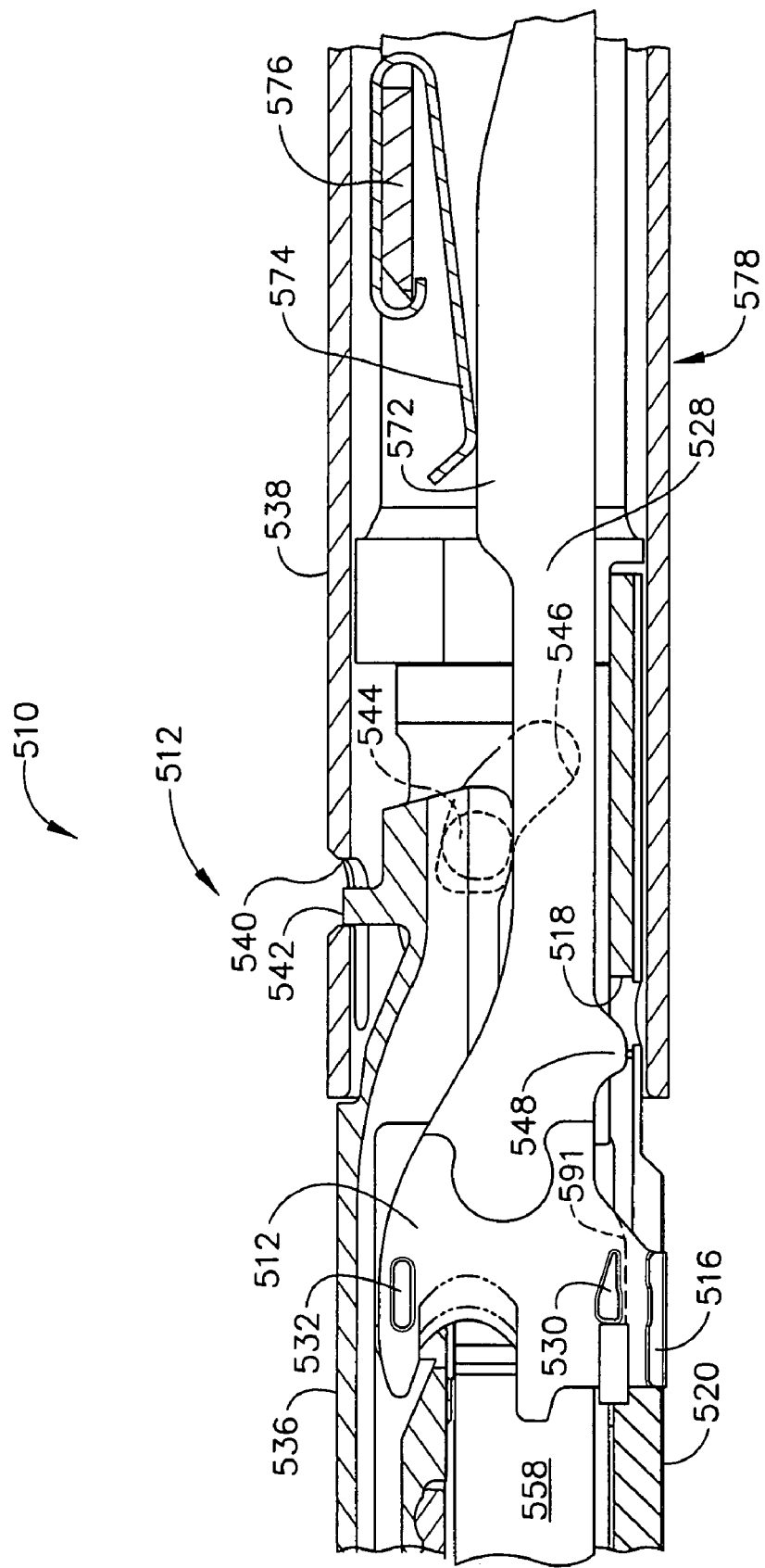
FIG. 37 is a left side view in elevation of the alternative implement portion, which now includes a spent staple cartridge, depicting an EAP actuated lockout mechanism taken in cross-section along lines 36—36 of FIG. 35 depicting locking between the EAP actuated lockout mechanism and the E-beam/firing bar as firing has been attempted.
Figure 38:
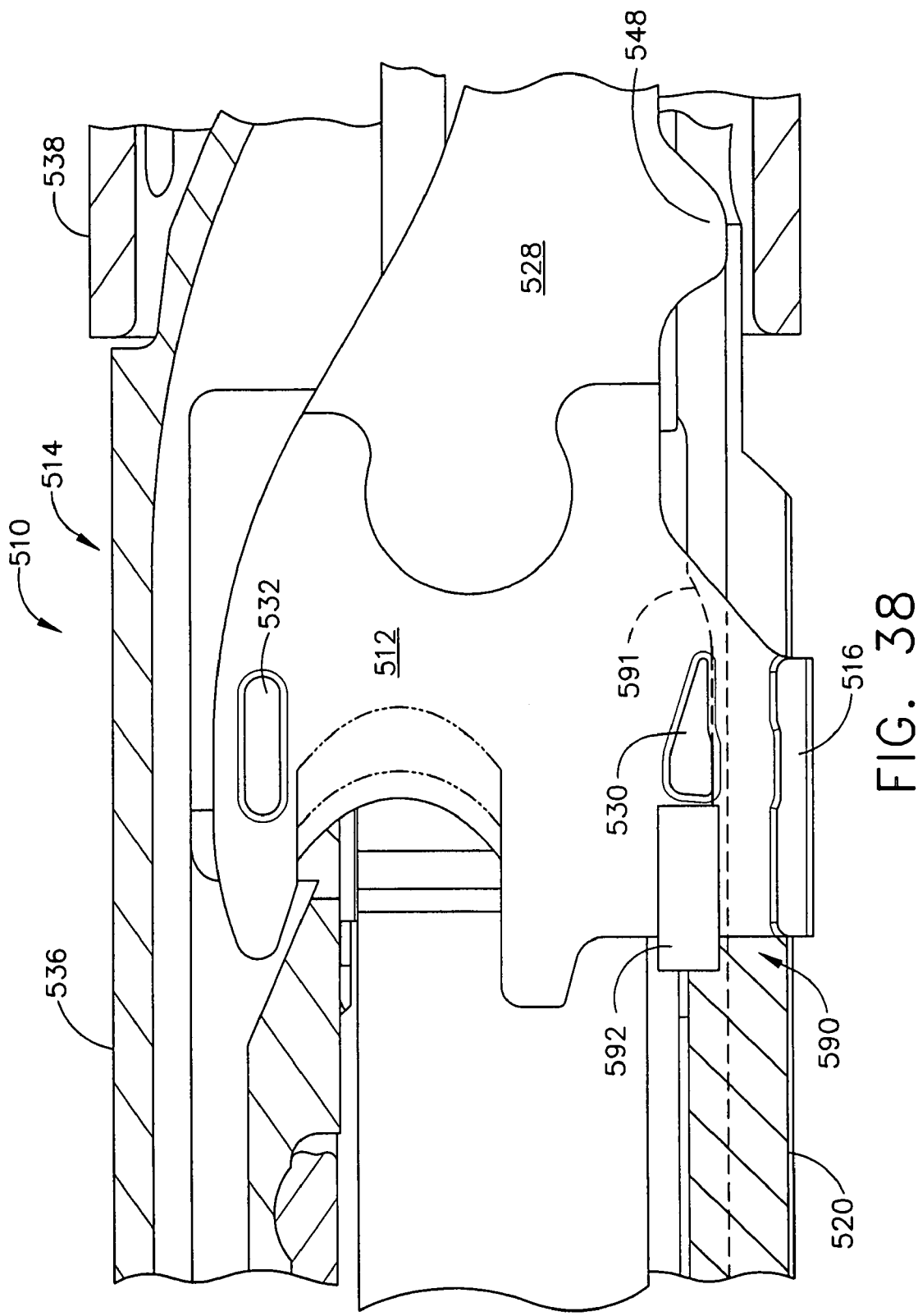
FIG. 38 is a left side detail view of the EAP actuated lockout mechanism and E-beam/firing bar of FIG. 37.

In FIGS. 37–38, the E-beam 512 has been distally moved as firing commences. The upper pins 532 enter a widened anvil track 552 formed in the anvil 536 that communicates with the anvil pocket 534. A narrowed anvil slot 554 that vertically communicates with the anvil track 552 allows passage of a cutting surface 556 of the E-beam 512 that severs tissue clamped between the anvil 536 and a staple cartridge 558 engaged to the staple channel 520. An engagement surface 560 of the E-beam 512 between the cutting surface 556 and middle pins 530 abuts a wedge sled 562 (FIG. 36) that is integral to and initially proximally positioned in the staple cartridge 558. It should be appreciated that the wedge sled 562 cams upwardly staple drivers 564 and thus staples 566 that sit onto of the staple drivers 564 within staple apertures 568 for forming against the anvil 536.

A more distal, heightened portion 572 of the firing bar 528 receives a downward urging by a clip spring 574 engaged to a frame 576 of an elongate shaft 578 of an implement portion 580 of the surgical stapling and severing instrument 510. The contact between the clip spring 574 and the heightened portion 572 is registered to each other during a first portion of firing travel in correspondence to the downward projection 548 dropping into the widened hole 518 and the middle pins 530 approaching the EAP actuated lockout mechanism 550. Thus, the clip spring 574 assists during this portion of firing travel in driving the middle pin 530 downward into a ramped recess 591 formed in the staple channel 520. In FIGS. 35–38, the EAP actuated lockout mechanism 590 includes an EAP vertically-expansive actuator 592 that receives an electrical excitation signal from a handle portion (not shown) to deactivate the EAP actuated lockout mechanism 590 to vertically compress to clear the way for one or both of the middle pin 530 and lower foot 516.

EAP Actuated Locking Mechanism with Downward Deflected, Abutting EAP Plate Actuator.

Figure 39:
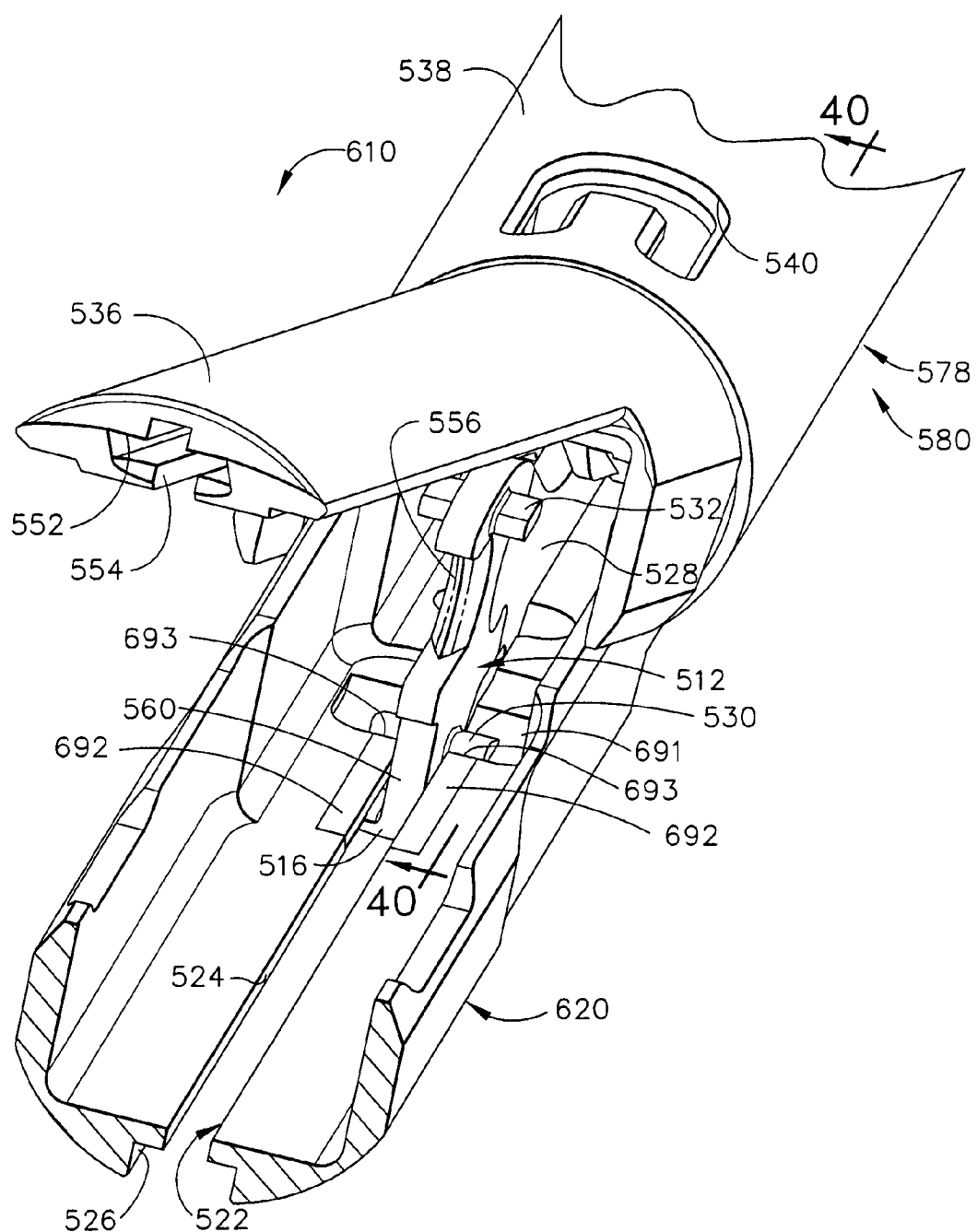
FIG. 39 is a front perspective, partially cutaway view of a second alternative implement portion for a surgical severing and stapling instrument, which has a staple cartridge removed, that incorporates an EAP actuated lockout mechanism.
Figure 40:
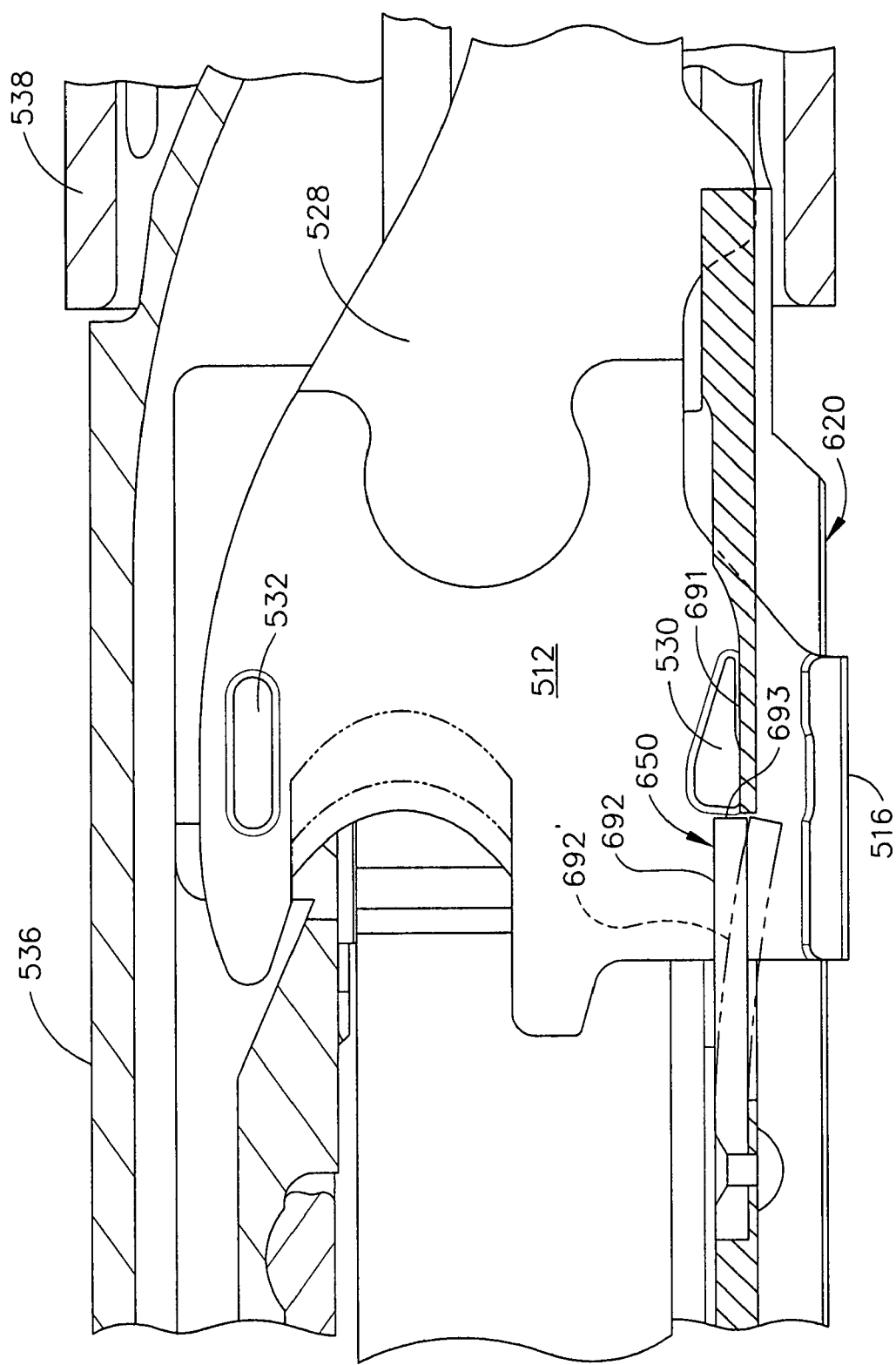
FIG. 40 is a left side view in elevation of the second alternative implement portion, which now includes a spent staple cartridge, depicting an EAP actuated lockout mechanism taken in cross-section along lines 40—40 of FIG. 39 depicting locking between the EAP actuated lockout mechanism and the E-beam/firing bar as firing has been attempted.

In FIGS. 39–40, a surgical stapling and severing instrument 610 is identical to that described for FIGS. 35–38 above except that an EAP actuated locking mechanism 650 utilizes a pair of proximally projecting, downwardly actuated EAP plate actuators 692 that are normally aligned to block respective ramped recesses 691 formed in a staple channel 620 and may be activated to bend downwardly into alignment with the respective ramped recess 691 (shown in phantom in FIG. 40 as 692'). Thus, a proximal end of the EAP plate actuator 692 presents an abutting surface 693 to absorb the firing forces from the middle pin 530, and thus the E-beam 512.

Figure 41:
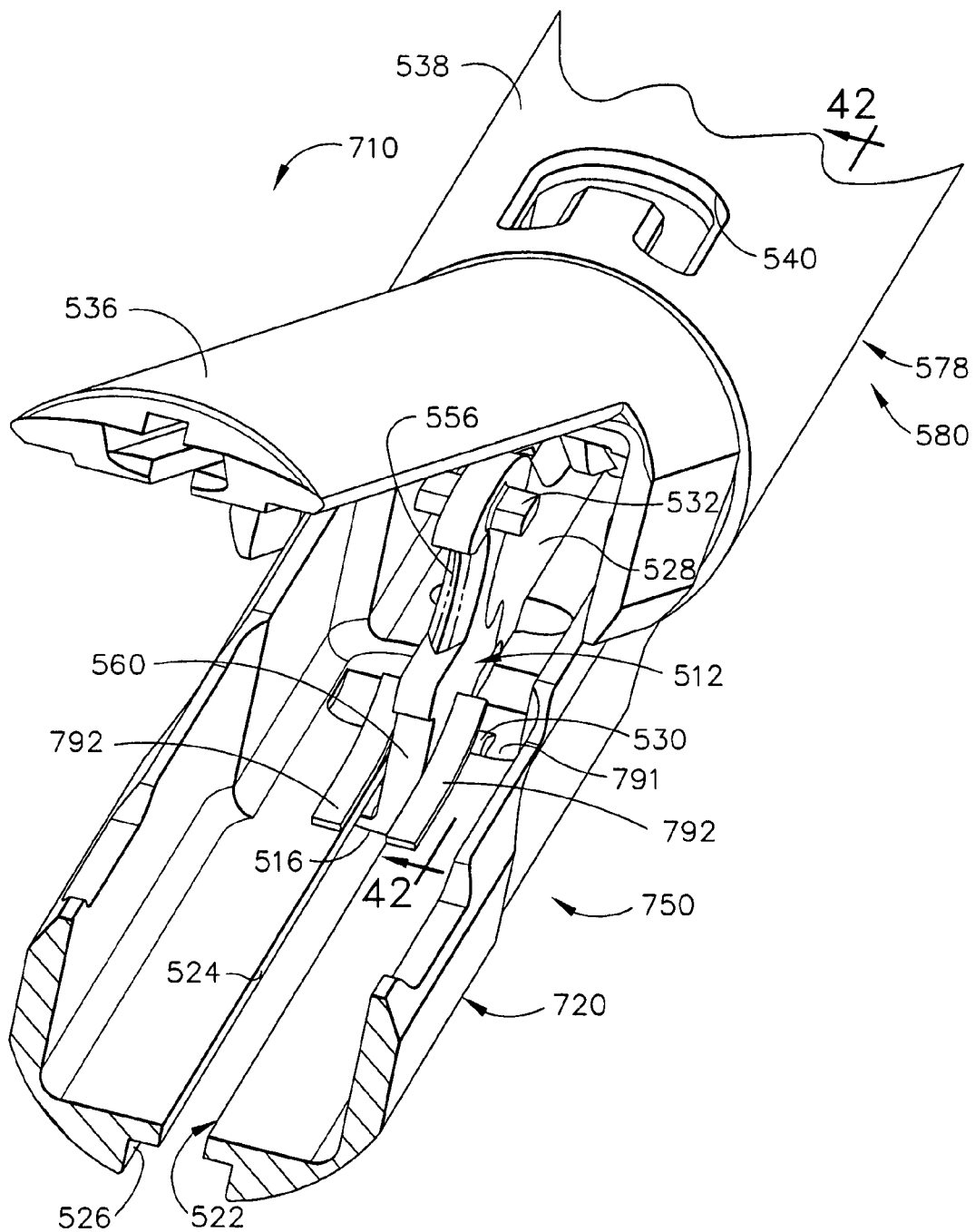
FIG. 41 is front perspective, partially cutaway view of a third alternative implement portion for a surgical severing and stapling instrument, which has a staple cartridge removed, that incorporates an EAP actuated lockout mechanism.
Figure 42:
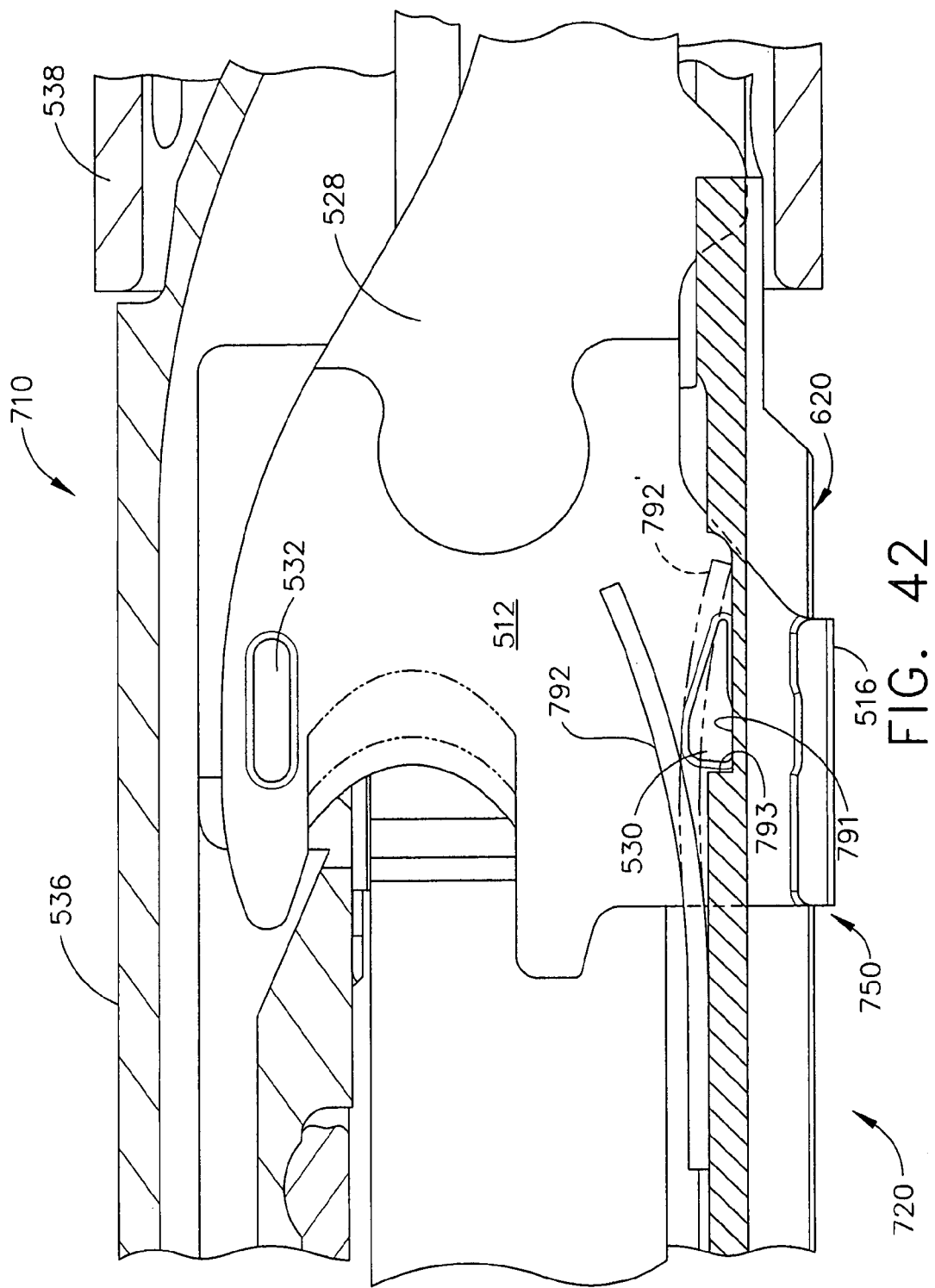
FIG. 42 is a left side view in elevation of the second alternative implement portion, which now includes a spent staple cartridge, depicting an EAP actuated lockout mechanism taken in cross-section along lines 42—42 of FIG. 41 depicting locking between the EAP actuated lockout mechanism and the E-beam/firing bar as firing has been attempted.

In FIGS. 41–42, a surgical stapling and severing instrument 710 is identical to that described for FIGS. 35–38 above except that an EAP actuated locking mechanism 750 utilizes a proximally projecting, downwardly actuated EAP plate actuator 792 that is normally aligned as a trapdoor to open a ramped recess 791 formed in a staple channel 720 and may be activated to bend downwardly to close the ramped recess 791 (shown in phantom in FIG. 40 as 792') to allow firing. Thus, an abutting surface 793 at a distal end of the ramped recess absorbs the firing forces from the middle pin 530 of the E-beam 512, preventing firing.

EAP Actuator Control Circuitry.

It should be appreciated that control circuitry in the handle portion may advantageously respond to or in anticipation of a user's firing command by deactivating an EAP lockout when deemed advisable. For example, a sensed missing staple cartridge, expended staple cartridge, or missized staple cartridge for the end effector may preclude a deactivation signal from reaching the EAP lockout or be sensed and interpreted by control logic in the handle portion. As another example, improperly clamped tissue may be sensed (e.g., pressure transducers spaced along the jaws may sense too much tissue or too little tissue along some portion of the end effector. In addition, for an end effector incorporating buttress material for thin or thick tissue, the presence or absence of buttress material when the contrary is warranted may preclude disengaging the lockout.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, a mechanical single lockout mechanism may comprise a spring-loaded plunger encompassed within the staple channel 16 that moves upwardly into the firing drive slot 47 when not contacted by the wedge sled 218 with the plunger presenting a hooked or otherwise.

As another example, although EAP actuator control circuitry is described that defaults to a locking condition when unpowered, it should be appreciated that this arrangement is illustrative. Applications consistent with aspects of the invention may default to an unlocked state with energy of one or more EAP actuator to move them to a locking state.

As yet a further example, while a detachable staple cartridge is described in the illustrative version, applications consistent with the present invention may include an interchangeable implement portion wherein the EAP lockout mechanism may be contained, at least partially, in the distal, interchangeable portion. Alternatively, a portion of the firing bar or firing rod proximal to the end effector may include a contacting surface that is selectively blocked by an EAP lockout mechanism proximal to the end effector.

What is claimed is:

1. A surgical instrument, comprising:
    a handle portion operably configured to produce a firing motion;
    an elongate shaft attached to the handle portion;
    a firing bar received for reciprocating longitudinal motion in the elongate shaft to transfer the firing motion;
    an end effector distally attached to the elongate shaft, forming an implement portion, the end effector responsive to the firing bar to perform a surgical operation;
    control circuitry operably configured to produce a firing signal; and
    an electrical lockout mechanism positioned in the implement portion responsive to the firing signal to change state between a blocking position and a nonblocking position to the firing bar.

2. The surgical instrument of claim 1, wherein the electrical lockout mechanism further comprises an electroactive polymer actuator.

3. The surgical instrument of claim 2, wherein the firing bar includes a lateral surface ramped to override when retracted the electrical lockout mechanism when in a blocking position.

4. The surgical instrument of claim 2, wherein the electroactive polymer actuator comprises a stack actuator positioned to actuate transverse to an axis of motion of the firing bar.

5. The surgical instrument of claim 2, wherein the electroactive polymer actuator comprises a proximally directed lockout finger operatively configured to actuate and relax between a raised and a lowered position.

6. The surgical instrument of claim 5, wherein the implement portion includes an inwardly directed recess positioned to receive the proximally directed lockout finger when in the lowered position allowing the firing bar to distally translate thereover wherein a proximal end of the proximally directed lockout finger is aligned to abut the firing bar when in the raised position.

7. The surgical instrument of claim 5, further comprising a transverse contact surface attached to the firing bar, the end effector including a recess registered to receive the transverse contact surface during an initial portion of firing travel, the elongate shaft further comprises an opposing bias on the firing bar urging the contact surface thereof into the end effector recess, the proximally directed lockout finger is positioned to close the recess to the contact surface and to direct the contact surface into the recess.

8. The surgical instrument of claim 7, further comprising a rigid substrate laminated to the electroactive polymer actuator.

9. A surgical instrument comprising:
    a handle portion operably configured to produce a firing motion;
    an staple channel coupled to the handle portion;
    an anvil pivotally attached to the staple channel;
    a staple device engaged by the staple channel and including a plurality of staple drivers to cam the staple drivers toward the anvil;
    a wedge member proximal to and longitudinally aligned with the staple drivers;
    a firing device responsive to the firing motion to drive the wedge member distally;
    a lockout device positioned in the staple channel and operably configured to actuate in response to an electrical signal to prevent distal movement of the firing device.

10. The surgical instrument of claim 9, wherein the staple device includes a firing drive slot through which at least a portion of the firing device distally traverses to drive the wedge member, the lockout device selectively intruding into the firing drive slot from the staple channel.

11. The surgical instrument of claim 10, wherein the electroactive polymer actuator comprises a stack actuator operatively configured to expand inwardly in response to an electrical signal.

12. The surgical instrument of claim 10, wherein the staple channel includes a ramped recess proximal to the electroactive polymer actuator, the electroactive polymer actuator further comprising a proximally directed beam operatively configured to activate by bending toward the ramped recess.

13. The surgical instrument of claim 12, wherein the proximally directed beam is positioned to activate to present an abutting surface to the firing member.

14. The surgical instrument of claim 12, wherein the proximally directed beam is positioned to activate to direct a portion of the firing member into the ramped recess, the ramped recess including a distal abutting surface.

15. The surgical instrument of claim 9, wherein the lockout device comprises an electroactive polymer actuator.

16. The surgical instrument of claim 9, wherein the firing device includes laterally projecting middle pin and lower foot that opposing engage each side of the staple channel, the lockout device laterally offset to selectively abut the middle pin.

17. The surgical instrument of claim 9, wherein the elongate shaft further comprises a closure sleeve proximally attached to the handle portion to receive a closure motion and distally attached to a pivot feature on the anvil to effect closure thereof.

18. A surgical instrument, comprising:
a handle portion operably configured to produce a firing motion;
an elongate shaft attached to the handle portion;
a firing bar received for reciprocating longitudinal motion in the elongate shaft to transfer the firing motion;
an end effector distally attached to the elongate shaft, forming an implement portion, the end effector responsive to the firing bar to perform a surgical operation;
a means for electrically actuating a firing bar lockout device in the implement portion positioned to block the firing bar.

* * * * *